US010366269B2

(12) United States Patent
Lu et al.

(10) Patent No.: US 10,366,269 B2
(45) Date of Patent: Jul. 30, 2019

(54) BIOMETRIC SYSTEM WITH PHOTOACOUSTIC IMAGING

(71) Applicant: QUALCOMM Incorporated, San Diego, CA (US)

(72) Inventors: Yipeng Lu, Davis, CA (US); David William Burns, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 124 days.

(21) Appl. No.: 15/149,048

(22) Filed: May 6, 2016

(65) Prior Publication Data

US 2017/0323132 A1     Nov. 9, 2017

(51) Int. Cl.
*G06K 9/00* (2006.01)
*A61B 5/00* (2006.01)
(Continued)

(52) U.S. Cl.
CPC .......... *G06K 9/0002* (2013.01); *A61B 5/0095* (2013.01); *A61B 5/14542* (2013.01); *A61B 5/6898* (2013.01); *G06K 9/00093* (2013.01); *G06K 9/00107* (2013.01); *G06K 9/00201* (2013.01); *G06K 9/4638* (2013.01); *A61B 5/14532* (2013.01); *A61B 5/14546* (2013.01);
(Continued)

(58) Field of Classification Search
None
See application file for complete search history.

(56) References Cited

U.S. PATENT DOCUMENTS 5,689,576 A * 11/1997 Schneider ........... G01S 7/52061
                                                         382/124
6,296,610 B1 * 10/2001 Schneider ............ A61B 5/1172
                                                         600/445
(Continued)

FOREIGN PATENT DOCUMENTS

JP          2015-142740        8/2015
KR           100722593         5/2007
(Continued)

OTHER PUBLICATIONS

International Search Report and Written Opinion—PCT/US2017/026196—ISA/EPO—dated Aug. 11, 2017.
(Continued)

*Primary Examiner* — Iman K Kholdebarin
(74) *Attorney, Agent, or Firm* — Weaver Austin Villeneuve & Sampson LLP

(57) ABSTRACT

An apparatus may include an ultrasonic sensor array, a light source system and a control system. Some implementations may include an ultrasonic transmitter. The control system may be operatively configured to control the light source system to emit light that induces acoustic wave emissions inside a target object. The control system may be operatively configured to select a first acquisition time delay for the reception of acoustic wave emissions primarily from a first depth inside the target object. The control system may be operatively configured to acquire first ultrasonic image data from the acoustic wave emissions received by the ultrasonic sensor array during a first acquisition time window. The first acquisition time window may be initiated at an end time of the first acquisition time delay.

32 Claims, 17 Drawing Sheets

(51) Int. Cl.
   *A61B 5/145*     (2006.01)
   *G06K 9/46*      (2006.01)
(52) U.S. Cl.
   CPC ..... *A61B 5/7225* (2013.01); *A61B 2562/0204* (2013.01); *A61B 2562/0242* (2013.01); *G06K 2009/00932* (2013.01)

(56) References Cited

U.S. PATENT DOCUMENTS

| | | | |
|---|---|---|---|
| 7,415,139 B2* | 8/2008 | Takiguchi | G06K 9/00013 382/115 |
| 7,515,948 B1* | 4/2009 | Balberg | A61B 5/0095 600/323 |
| 8,201,739 B2* | 6/2012 | Schneider | G06K 9/0002 235/439 |
| 9,833,216 B2* | 12/2017 | Ohuchi | A61B 8/0841 |
| 9,855,024 B2* | 1/2018 | Ohuchi | A61B 8/5284 |
| 2002/0138743 A1 | 9/2002 | Murakami et al. | |
| 2006/0213273 A1* | 9/2006 | Lasser | G01N 29/07 73/606 |
| 2007/0179365 A1* | 8/2007 | Bitton | A61B 5/0059 600/310 |
| 2010/0329425 A1* | 12/2010 | Guo | G01T 1/247 378/91 |
| 2011/0098550 A1* | 4/2011 | Yoda | A61B 5/0059 600/407 |
| 2011/0215150 A1 | 9/2011 | Schneider et al. | |
| 2012/0177257 A1 | 7/2012 | Maev et al. | |
| 2013/0063399 A1 | 3/2013 | Noro et al. | |
| 2013/0237859 A1 | 9/2013 | Taku | |
| 2014/0070082 A1* | 3/2014 | Guo | G01N 21/59 250/227.14 |
| 2014/0100438 A1* | 4/2014 | Wada | A61B 5/0095 600/407 |
| 2014/0219521 A1* | 8/2014 | Schmitt | G06K 9/0002 382/124 |
| 2014/0355376 A1* | 12/2014 | Schneider | G01S 7/56 367/7 |
| 2015/0094569 A1* | 4/2015 | Ohuchi | A61B 8/0841 600/424 |
| 2015/0116249 A1 | 4/2015 | Han et al. | |
| 2015/0201902 A1* | 7/2015 | Zhu | A61B 8/12 600/443 |
| 2015/0265156 A1* | 9/2015 | Tanaka | A61B 5/0095 600/473 |
| 2015/0342571 A1* | 12/2015 | Ohuchi | A61B 8/0883 382/128 |
| 2016/0033354 A1* | 2/2016 | Li | G01M 3/243 73/40.5 A |
| 2016/0157830 A1 | 6/2016 | Katsuyama | |
| 2017/0057438 A1 | 3/2017 | Dow et al. | |
| 2017/0090024 A1* | 3/2017 | Kitchens, II | G01S 7/539 |
| 2017/0090028 A1* | 3/2017 | Djordjev | G01S 15/89 |
| 2017/0112383 A1 | 4/2017 | Milione et al. | |
| 2017/0172419 A1* | 6/2017 | Oishi | A61B 5/0095 |
| 2017/0188991 A1* | 7/2017 | Boctor | A61B 8/0841 |
| 2017/0234736 A1* | 8/2017 | Quere | G01J 3/453 356/520 |
| 2017/0281121 A1* | 10/2017 | Dahl | G01S 7/52036 |
| 2017/0323131 A1 | 11/2017 | Lu et al. | |
| 2018/0055369 A1* | 3/2018 | Burns | A61B 5/0095 |

FOREIGN PATENT DOCUMENTS

| | | |
|---|---|---|
| WO | 2014178257 A1 | 11/2014 |
| WO | 2015/009635 | 1/2015 |
| WO | 2016051749 A1 | 4/2016 |

OTHER PUBLICATIONS

International Search Report and Written Opinion—PCT/US2017/026203—ISA/EPO—dated Jun. 30, 2017.
Partial International Search Report—PCT/US2017/026196—ISA/EPO—dated Jun. 21, 2017.
U.S. Office Action dated Mar. 7, 2018 in U.S. Appl. No. 15/149,046.
Second Written Opinion—PCT/US2017/026203—ISA-EPO—dated Apr. 9, 2018.
U.S. Notice of Allowance dated Jul. 27, 2018 in U.S. Appl. No. 15/149,046.
U.S. Notice of Allowance dated Nov. 1, 2018 in U.S. Appl. No. 15/149,046.

* cited by examiner

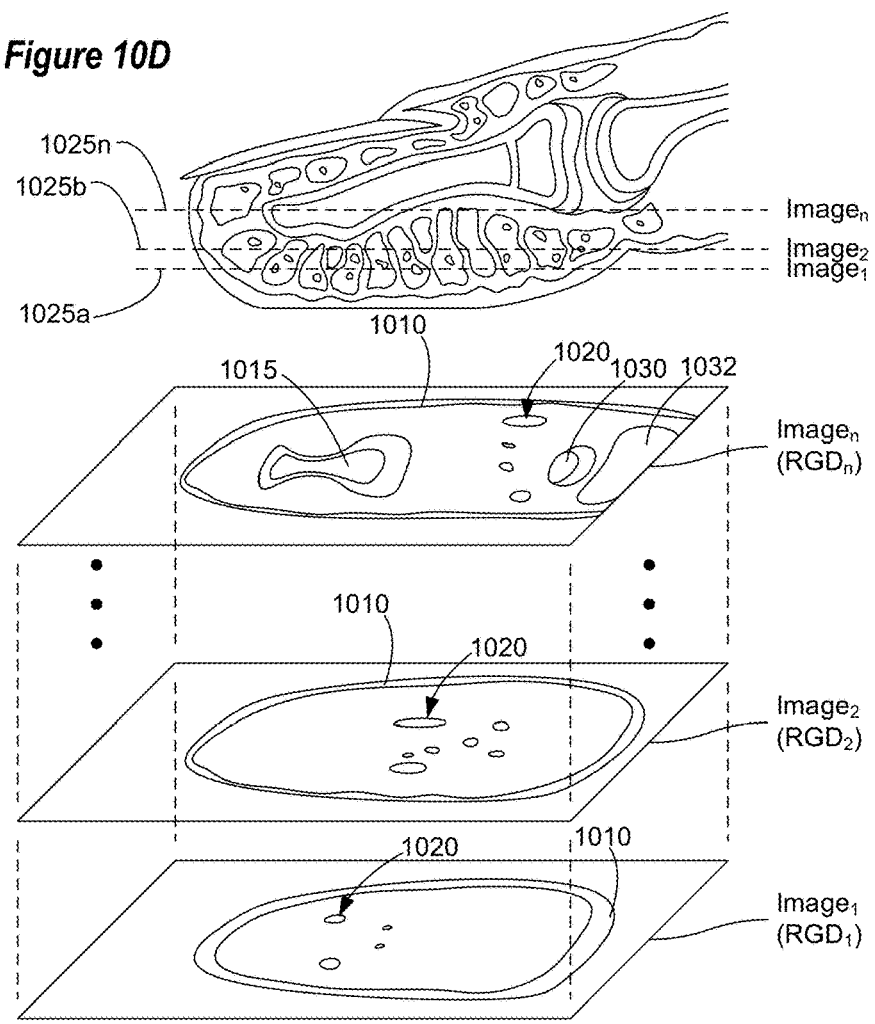
*Figure 10D*
*Figure 10E*
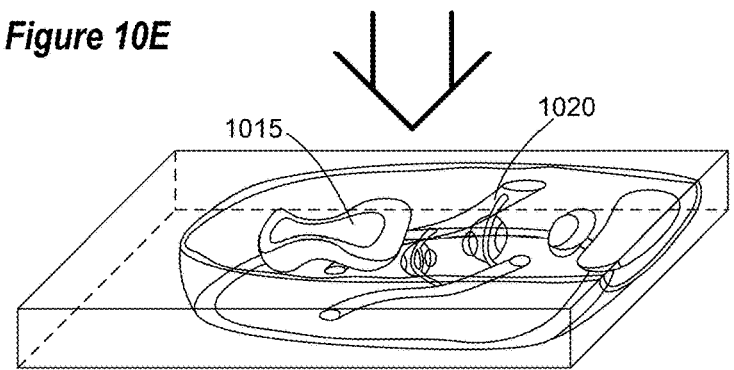
*Figure 10F*

BIOMETRIC SYSTEM WITH PHOTOACOUSTIC IMAGING

TECHNICAL FIELD

This disclosure relates generally to biometric devices and methods, including but not limited to biometric devices and methods applicable to mobile devices.

DESCRIPTION OF THE RELATED TECHNOLOGY

As mobile devices become more versatile, user authentication becomes increasingly important. Increasing amounts of personal information may be stored on and/or accessible by a mobile device. Moreover, mobile devices are increasingly being used to make purchases and perform other commercial transactions. Some mobile devices, including but not limited to smartphones, currently include fingerprint sensors for user authentication. However, some fingerprint sensors are easily spoofed. Improved authentication methods would be desirable.

SUMMARY

The systems, methods and devices of the disclosure each have several innovative aspects, no single one of which is solely responsible for the desirable attributes disclosed herein.

One innovative aspect of the subject matter described in this disclosure can be implemented in an apparatus. The apparatus may include a substrate, an ultrasonic sensor array on or proximate the substrate, a light source system and a control system. In some examples, the apparatus may be, or may include, a biometric system. In some implementations, a mobile device may be, or may include, the apparatus. For example, a mobile device may include a biometric system as disclosed herein.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be capable of controlling the light source system to emit light and of receiving signals from the ultrasonic sensor array corresponding to acoustic waves emitted from portions of a target object. The emissions may be due to the target object being illuminated with light emitted by the light source system. The control system may be capable of performing a user authentication process that is based, at least in part, on the signals from the ultrasonic sensor array.

The apparatus may or may not include an ultrasonic transmitter, depending on the particular implementation. If the apparatus includes an ultrasonic transmitter, the control system may be capable of controlling the ultrasonic transmitter to obtain fingerprint image data via the ultrasonic sensor array. The authentication process may involve evaluating the fingerprint image data.

In some examples, the light source system may include one or more laser diodes or light-emitting diodes. For example, the light source system may include at least one infrared, optical, red, green, blue, white or ultraviolet light-emitting diode and/or at least one infrared, optical, red, green, blue or ultraviolet laser diode. In some implementations, the light source system may be capable of emitting a light pulse with a pulse width less than about 100 nanoseconds. In some examples, the light source system may be capable of emitting a plurality of light pulses at a pulse frequency between about 1 MHz and about 100 MHz. The pulse frequency of the plurality of light pulses may, in some instances, correspond to an acoustic resonant frequency of the ultrasonic sensor array and/or the substrate. According to some implementations, the light emitted by the light source system may be transmitted through the substrate. According to some examples, the control system may be capable of selecting one or more acquisition time delays to receive acoustic wave emissions from one or more corresponding distances from the ultrasonic sensor array.

In some implementations, the control system may be capable of selecting a wavelength of the light emitted by the light source system. According to some such implementations, the control system may be capable of selecting the wavelength and a light intensity associated with the selected wavelength to illuminate portions of the target object.

According to some examples, the control system may be capable of comparing, for the purpose of user authentication, attribute information with stored attribute information obtained from image data that has previously been received from an authorized user. The attribute information may be obtained from received image data, based on the signals from the ultrasonic sensor array. In some examples, the attribute information obtained from the received image data and the stored attribute information may include attribute information corresponding to at least one of sub-epidermal features, muscle tissue features or bone tissue features. In some implementations, the attribute information obtained from the received image data and the stored attribute information may include attribute information corresponding to sub-epidermal features. In some such implementations, the sub-epidermal features may include features of the dermis, features of the subcutis, blood vessel features, lymph vessel features, sweat gland features, hair follicle features, hair papilla features and/or fat lobule features. Alternatively, or additionally, the attribute information obtained from the received image data and the stored attribute information may include information regarding fingerprint minutia.

In some examples, the control system may be capable of, for the purpose of user authentication, obtaining ultrasonic image data via insonification of the target object with ultrasonic waves from an ultrasonic transmitter. The control system may be capable of obtaining ultrasonic image data via illumination of the target object with light emitted from the light source system. In some such examples, the ultrasonic image data obtained via insonification of the target object may include fingerprint image data. Alternatively, or additionally, the ultrasonic image data obtained via illumination of the target object may include vascular image data.

According to some implementations, the target object may be positioned on a surface of the ultrasonic sensor array or positioned on a surface of a platen that is acoustically coupled to the ultrasonic sensor array. In some examples, the target object may be a finger or a finger-like object. According to some implementations, the control system may be configured to make a liveness determination of the target object based on the received signals.

Other innovative aspects of the subject matter described in this disclosure can be implemented in a biometric authentication method that may involve controlling a light source system to emit light. The method may involve receiving signals from an ultrasonic sensor array corresponding to acoustic waves emitted from portions of a target object in response to being illuminated with light emitted by the light source system. The method may involve performing a user authentication process that is based, at least in part, on the signals from the ultrasonic sensor array.

In some examples, the method may involve obtaining ultrasonic image data via insonification of the target object with ultrasonic waves from an ultrasonic transmitter. The user authentication process may be based, at least in part, on the ultrasonic image data.

In some instances, the method may involve selecting a wavelength and a light intensity of the light emitted by the light source system to selectively generate acoustic wave emissions from portions of the target object. In some examples, the method may involve selecting an acquisition time delay to receive acoustic wave emissions at a corresponding distance from the ultrasonic sensor array.

In some examples, controlling the light source system may involve controlling a light source system of a mobile device. In some such examples, controlling the light source system involves controlling at least one backlight or front light capable of illuminating a display of the mobile device.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in a non-transitory medium having software stored thereon.

For example, the software may include instructions for controlling a light source system to emit light. The software may include instructions for receiving signals from an ultrasonic sensor array corresponding to acoustic waves emitted from portions of a target object in response to being illuminated with light emitted by the light source system. The software may include instructions for performing a user authentication process that is based, at least in part, on the signals from the ultrasonic sensor array.

According to some examples, the software may include instructions for obtaining ultrasonic image data via insonification of the target object with ultrasonic waves from an ultrasonic transmitter. The user authentication process may be based, at least in part, on the ultrasonic image data. In some instances, the software may include instructions for selecting a wavelength and a light intensity of the light emitted by the light source system to selectively generate acoustic wave emissions from portions of the target object. In some examples, the software may include instructions for selecting an acquisition time delay to receive acoustic wave emissions at a corresponding distance from the ultrasonic sensor array. According to some implementations, controlling the light source system may involve controlling at least one backlight or front light capable of illuminating a display of a mobile device.

Other innovative aspects of the subject matter described in this disclosure also can be implemented in an apparatus. The apparatus may include an ultrasonic sensor array, a light source system and a control system. In some examples, the apparatus may be, or may include, a biometric system. In some implementations, a mobile device may be, or may include, the apparatus. For example, a mobile device may include a biometric system as disclosed herein. In some implementations, the ultrasonic sensor array and a portion of the light source system may be configured in an ultrasonic button, a display module and/or a mobile device enclosure.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be operatively configured to control the light source system to emit light that induces acoustic wave emissions inside a target object. The control system may be operatively configured to select a first acquisition time delay for the reception of acoustic wave emissions primarily from a first depth inside the target object. The control system may be operatively configured to acquire first ultrasonic image data from the acoustic wave emissions received by the ultrasonic sensor array during a first acquisition time window. The first acquisition time window may be initiated at an end time of the first acquisition time delay. In some implementations, the first ultrasonic image data may be acquired during the first acquisition time window from a peak detector circuit disposed in each of a plurality of sensor pixels within the ultrasonic sensor array.

In some examples, the apparatus may include a display. The control system may be configured to control the display to depict a two-dimensional image that corresponds with the first ultrasonic image data.

According to some examples, the acquisition time delay may be measured from a time that the light source system emits light. In some implementations, the first acquisition time window may be in the range of about 10 nanoseconds to about 200 nanoseconds. In some instances, the control system may be operatively configured to select second through $N^{th}$ acquisition time delays and to acquire second through $N^{th}$ ultrasonic image data during second through $N^{th}$ acquisition time windows after the second through $N^{th}$ acquisition time delays. Each of the second through $N^{th}$ acquisition time delays may correspond to a second through an $N^{th}$ depth inside the target object. In some such examples, the apparatus may include a display and the control system may be configured to control the display to depict a three-dimensional image that corresponds with at least a subset of the first through $N^{th}$ ultrasonic image data.

In some examples, the light source system may include one or more laser diodes, semiconductor lasers and/or light-emitting diodes. For example, the light source system may include at least one infrared, optical, red, green, blue, white or ultraviolet light-emitting diode and/or at least one infrared, optical, red, green, blue or ultraviolet laser diode. In some implementations, the light source system may be capable of emitting a light pulse with a pulse width less than about 100 nanoseconds. According to some implementations, the control system may be configured to control the light source system to emit at least one light pulse having a duration that is in the range of about 10 nanoseconds to about 500 nanoseconds. In some examples, the light source system may be capable of emitting a plurality of light pulses at a pulse frequency between about 1 MHz and about 100 MHz.

In some implementations, the apparatus may include a substrate. In some such implementations, the ultrasonic sensor array may be formed in or on the substrate. In some examples, the light source system may be coupled to the substrate. According to some implementations, the light emitted by the light source system may be transmitted through the substrate. In some examples, light emitted by the light source system may be transmitted through the ultrasonic sensor array. In some implementations, the light emitted by the light source system may include a plurality of light pulses and the pulse frequency of the plurality of light pulses may correspond to an acoustic resonant frequency of the ultrasonic sensor array and/or the substrate. According to some examples, the control system may be capable of selecting one or more acquisition time delays to receive acoustic wave emissions from one or more corresponding distances from the ultrasonic sensor array.

In some implementations, the control system may be capable of selecting a wavelength of the light emitted by the light source system. According to some such implementations, the control system may be capable of selecting the wavelength and a light intensity associated with the selected wavelength to illuminate portions of the target object. In some examples, the control system may be configured to select one or more wavelengths of the light to trigger acoustic wave emissions primarily from a particular type of material in the target object.

According to some examples, the control system may be capable of comparing, for the purpose of user authentication, attribute information obtained from received image data, based on the signals from the ultrasonic sensor array, with stored attribute information obtained from image data that has previously been received from an authorized user. In some examples, the attribute information obtained from the received image data and the stored attribute information may include attribute information corresponding to at least one of sub-epidermal features, muscle tissue features or bone tissue features. In some implementations, the attribute information obtained from the received image data and the stored attribute information may include attribute information corresponding to sub-epidermal features. In some such implementations, the sub-epidermal features may include features of the dermis, features of the subcutis, blood vessel features, lymph vessel features, sweat gland features, hair follicle features, hair papilla features and/or fat lobule features. Alternatively, or additionally, the attribute information obtained from the received image data and the stored attribute information may include information regarding fingerprint minutia.

In some examples, the control system may be capable of, for the purpose of user authentication, obtaining ultrasonic image data via insonification of the target object with ultrasonic waves from an ultrasonic transmitter. The control system may be capable of obtaining ultrasonic image data via illumination of the target object with light emitted from the light source system. In some such examples, the ultrasonic image data obtained via insonification of the target object may include fingerprint image data. Alternatively, or additionally, the ultrasonic image data obtained via illumination of the target object may include vascular image data.

According to some implementations, the target object may be positioned on a surface of the ultrasonic sensor array or positioned on a surface of a platen that is acoustically coupled to the ultrasonic sensor array. In some examples, the target object may be a finger or a finger-like object. According to some implementations, the control system may be configured to make a liveness determination of the target object based on the received signals.

According to some implementations, controlling the light source system may involve controlling at least one backlight or front light capable of illuminating a display. The light source system may include at least one backlight or front light configured for illuminating the display and a target object. In some examples, controlling the light source system may involve controlling a light source system of a mobile device. In some such examples, controlling the light source system involves controlling at least one backlight or front light capable of illuminating a display of the mobile device.

In some examples, the control system may be configured to estimate a blood oxygen level. According to some implementations, the control system may be configured to estimate a blood glucose level.

In some examples, the control system may be configured to acquire second ultrasonic image data primarily from the first depth inside the target object. In some instances, the second ultrasonic image data may be acquired after a period of time corresponding to a frame rate.

In some implementations, the control system may be configured for image stitching. For example, in some such implementations, the control system may be configured to acquire second ultrasonic image data at primarily the first depth inside the target object. The second ultrasonic image data may be acquired after the target object is repositioned on the apparatus or after the apparatus has been repositioned with respect to the target object. In some implementations, the control system may be configured to stitch together the first and second ultrasonic image data to form a composite ultrasonic image.

The apparatus may or may not include an ultrasonic transmitter, depending on the particular implementation. If the apparatus includes an ultrasonic transmitter, the control system may be configured to acquire second ultrasonic image data from insonification of the target object with ultrasonic waves from the ultrasonic transmitter. In some such examples, the second ultrasonic image data may be acquired primarily from the first depth inside the target object and the first ultrasonic image data and the second ultrasonic image data may be acquired from a plurality of sensor pixels within the ultrasonic sensor array. In some examples, the control system may be capable of controlling the ultrasonic transmitter to obtain fingerprint image data via the ultrasonic sensor array. The authentication process may involve evaluating the fingerprint image data and/or evaluating date that is based on the fingerprint image data, such as fingerprint minutiae.

Still other innovative aspects of the subject matter described in this disclosure can be implemented in a method of acquiring ultrasonic image data that involves controlling a light source system to emit light. The light may induce acoustic wave emissions inside a target object. The method may involve selecting a first acquisition time delay to receive the acoustic wave emissions primarily from a first depth inside the target object. The method may involve acquiring first ultrasonic image data from the acoustic wave emissions received by a ultrasonic sensor array during a first acquisition time window. The first acquisition time window may be initiated at an end time of the first acquisition time delay. In some examples, the method may involve controlling a display to depict a two-dimensional image that corresponds with the first ultrasonic image data.

In some examples, the acquisition time delay may be measured from a time that the light source system emits light. In some instances, the first acquisition time window may be in the range of about 10 nanoseconds to about 200 nanoseconds.

In some examples, the method may involve selecting second through $N^{th}$ acquisition time delays and acquiring second through $N^{th}$ ultrasonic image data during second through $N^{th}$ acquisition time windows after the second through $N^{th}$ acquisition time delays. In some such examples, each of the second through $N^{th}$ acquisition time delays may correspond to a second through an $N^{th}$ depth inside the target object.

Yet other innovative aspects of the subject matter described in this disclosure can be implemented in a non-transitory medium having software stored thereon. In some examples, the software may include instructions for controlling one or more devices to control a light source system to emit light. The light may induce acoustic wave emissions inside a target object. The software may include instructions for selecting a first acquisition time delay to receive the acoustic wave emissions primarily from a first depth inside the target object. The software may include instructions for acquiring first ultrasonic image data from the acoustic wave emissions received by a ultrasonic sensor array during a first acquisition time window. In some examples, the software may include instructions for controlling a display to depict a two-dimensional image that corresponds with the first ultrasonic image data.

The first acquisition time window may, for example, be initiated at an end time of the first acquisition time delay. In some examples, the acquisition time delay is measured from a time that the light source system emits light. According to some implementations, the first acquisition time window may be in the range of about 10 nanoseconds to about 200 nanoseconds. In some examples, the software may include instructions for selecting second through $N^{th}$ acquisition time delays and for acquiring second through $N^{th}$ ultrasonic image data during second through $N^{th}$ acquisition time windows after the second through $N^{th}$ acquisition time delays. Each of the second through $N^{th}$ acquisition time delays may correspond to a second through an $N^{th}$ depth inside the target object.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

FIGS. 10D-10F show a series of simplified two-dimensional images and a three-dimensional reconstruction that correspond with ultrasonic image data acquired by the processes shown in FIGS. 10A-10C.

DETAILED DESCRIPTION

Figure 1:
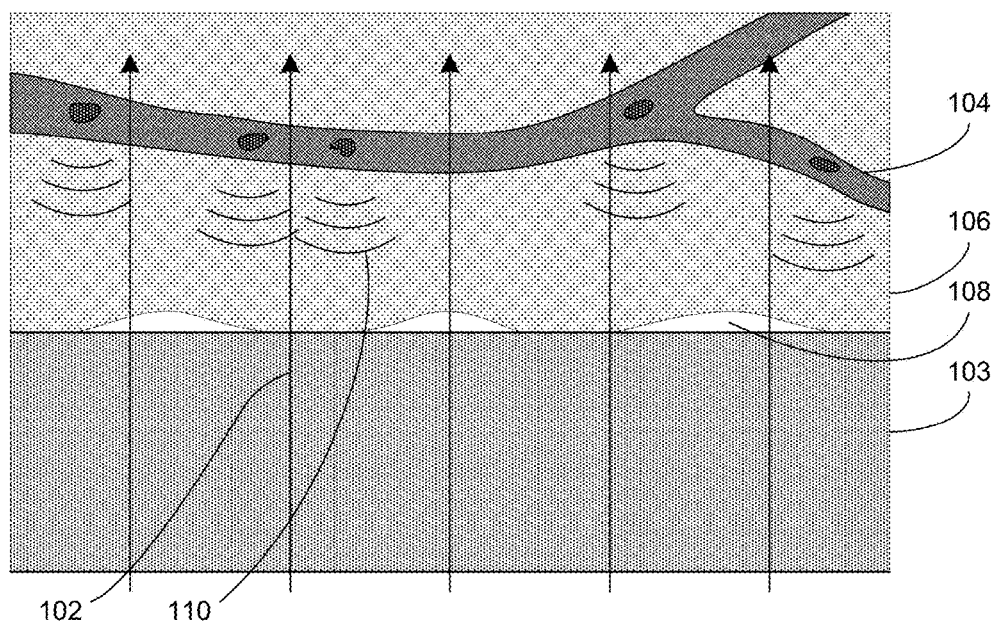
FIG. 1 shows an example of components of blood being differentially heated by incident light and subsequently emitting acoustic waves.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a biometric system as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Various implementations disclosed herein may include a biometric system that is capable of optical excitation and ultrasonic imaging of resultant acoustic wave generation. Such imaging may be referred to herein as "photoacoustic imaging." Some such implementations may be capable of obtaining images from bones, muscle tissue, blood, blood vessels, and/or other sub-epidermal features. As used herein, the term "sub-epidermal features" may refer to any of the tissue layers that underlie the epidermis, including the dermis, the subcutis, etc., and any blood vessels, lymph vessels, sweat glands, hair follicles, hair papilla, fat lobules, etc., that may be present within such tissue layers. Some implementations may be capable of biometric authentication that is based, at least in part, on image data obtained via photoacoustic imaging. In some examples, an authentication process may be based on image data obtained via photoacoustic imaging and also on image data obtained by transmitting ultrasonic waves and detecting corresponding reflected ultrasonic waves.

In some implementations, the incident light wavelength or wavelengths emitted by a light source system may be selected to trigger acoustic wave emissions primarily from a particular type of material, such as blood, blood cells, blood vessels, blood vasculature, lymphatic vasculature, other soft tissue, or bones. The acoustic wave emissions may, in some examples, include ultrasonic waves. In some such implementations, the control system may be capable of estimating a blood oxygen level, estimating a blood glucose level, or estimating both a blood oxygen level and a blood glucose level.

Alternatively, or additionally, the time interval between the irradiation time and the time during which resulting ultrasonic waves are sampled (which may be referred to herein as the acquisition time delay or the range-gate delay (RGD)) may be selected to receive acoustic wave emissions primarily from a particular depth and/or from a particular type of material. For example, a relatively larger range-gate delay may be selected to receive acoustic wave emissions primarily from bones and a relatively smaller range-gate delay may be selected to receive acoustic wave emissions primarily from sub-epidermal features (such as blood vessels, blood, etc.), muscle tissue features or bone tissue features.

Accordingly, some biometric systems disclosed herein may be capable of acquiring images of sub-epidermal features via photoacoustic imaging. In some implementations, a control system may be capable of acquiring first ultrasonic image data from acoustic wave emissions that are received by an ultrasonic sensor array during a first acquisition time window that is initiated at an end time of a first acquisition time delay. According to some examples, the control system may be capable of controlling a display to depict a two-dimensional (2-D) image that corresponds with the first ultrasonic image data. In some instances, the control system may be capable of acquiring second through $N^{th}$ ultrasonic image data during second through $N^{th}$ acquisition time windows after second through $N^{th}$ acquisition time delays. Each of the second through $N^{th}$ acquisition time delays may correspond to a second through an $N^{th}$ depth inside the target object. According to some examples, the control system may be capable of controlling a display to depict a three-dimensional (3-D) image that corresponds with at least a subset of the first through $N^{th}$ ultrasonic image data.

Particular implementations of the subject matter described in this disclosure can be implemented to realize one or more of the following potential advantages. Imaging sub-epidermal features (such as blood vessels, blood, etc.), muscle tissue features, etc., using ultrasonic technology alone can be challenging due to the small acoustic impedance contrast between various types of soft tissue. In some photoacoustic imaging implementations, a relatively higher signal-to-noise ratio may be obtained for the resulting acoustic wave emission detection because the excitation is via optical stimulation instead of (or in addition to) ultrasonic wave transmission. The higher signal-to-noise ratio can provide relatively more accurate and relatively more detailed imaging of blood vessels and other sub-epidermal features. In addition to the inherent value of obtaining more detailed images (e.g., for improved medical determinations and diagnoses), the detailed imaging of blood vessels and other sub-epidermal features can provide more reliable user authentication and liveness determinations. Moreover, some photoacoustic imaging implementations can detect changes in blood oxygen levels, which can provide enhanced liveness determinations. Some implementations provide a mobile device that includes a biometric system that is capable of some or all of the foregoing functionality. Some such mobile devices may be capable of displaying 2-D and/or 3-D images of sub-epidermal features, bone tissue, etc.

FIG. 1 shows an example of components of blood being differentially heated by incident light and subsequently emitting acoustic waves. In this example, incident light 102 has been transmitted from a light source system (not shown) through a substrate 103 and into a blood vessel 104 of an overlying finger 106. The surface of the finger 106 includes ridges and valleys, so some of the incident light 102 has been transmitted through the air 108 in this example. Here, the incident light 102 is causing optical excitation of illuminated blood and blood components in the blood vessel 104 and resultant acoustic wave generation. In this example, the generated acoustic waves 110 may include ultrasonic waves.

In some implementations, such acoustic wave emissions may be detected by sensors of a sensor array, such as the ultrasonic sensor array 202 that is described below with reference to FIG. 2. In some instances, the incident light wavelength, wavelengths and/or wavelength range(s) may be selected to trigger acoustic wave emissions primarily from a particular type of material, such as blood, blood components, blood vessels, other soft tissue, or bones.

Figure 2:
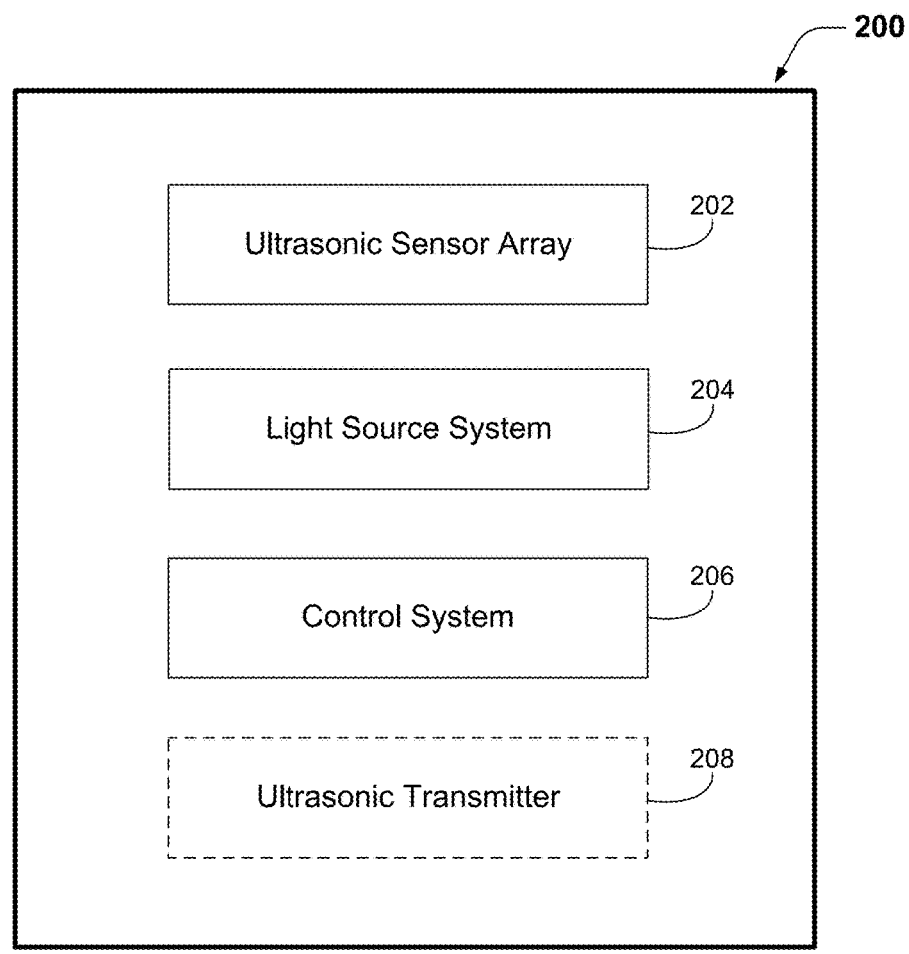
FIG. 2 is a block diagram that shows example components of an apparatus according to some disclosed implementations.

FIG. 2 is a block diagram that shows example components of an apparatus according to some disclosed implementations. In this example, the apparatus 200 includes a biometric system. Here, the biometric system includes an ultrasonic sensor array 202, a light source system 204 and a control system 206. Although not shown in FIG. 2, the apparatus 200 may include a substrate. Some examples are described below. Some implementations of the apparatus 200 may include the optional ultrasonic transmitter 208.

Various examples of ultrasonic sensor arrays 202 are disclosed herein, some of which may include an ultrasonic transmitter and some of which may not. Although shown as separate elements in FIG. 2, in some implementations the ultrasonic sensor array 202 and the ultrasonic transmitter 208 may be combined in an ultrasonic transceiver. For example, in some implementations, the ultrasonic sensor array 202 may include a piezoelectric receiver layer, such as a layer of PVDF polymer or a layer of PVDF-TrFE copolymer. In some implementations, a separate piezoelectric layer may serve as the ultrasonic transmitter. In some implementations, a single piezoelectric layer may serve as the transmitter and as a receiver. In some implementations, other piezoelectric materials may be used in the piezoelectric layer, such as aluminum nitride (AlN) or lead zirconate titanate (PZT). The ultrasonic sensor array 202 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some alternative examples, the ultrasonic sensor array 202 may be an ultrasonic receiver array and the ultrasonic transmitter 208 may include one or more separate elements. In some such examples, the ultrasonic transmitter 208 may include an ultrasonic plane-wave generator, such as those described below.

The light source system 204 may, in some examples, include an array of light-emitting diodes. In some implementations, the light source system 204 may include one or more laser diodes. According to some implementations, the light source system may include at least one infrared, optical, red, green, blue, white or ultraviolet light-emitting diode. In some implementations, the light source system 204 may include one or more laser diodes. For example, the light source system 204 may include at least one infrared, optical, red, green, blue or ultraviolet laser diode.

In some implementations, the light source system 204 may be capable of emitting various wavelengths of light, which may be selectable to trigger acoustic wave emissions primarily from a particular type of material. For example, because the hemoglobin in blood absorbs near-infrared light very strongly, in some implementations the light source system 204 may be capable of emitting one or more wavelengths of light in the near-infrared range, in order to trigger acoustic wave emissions from hemoglobin. However, in some examples the control system 206 may control the wavelength(s) of light emitted by the light source system 204 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic sensor array 202. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic sensor array. Image data from the ultrasonic sensor array that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength.

That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 204 may be capable of emitting a light pulse with a pulse width less than about 100 nanoseconds. In some implementations, the light pulse may have a pulse width between about 10 nanoseconds and about 500 nanoseconds or more. In some implementations, the light source system 204 may be capable of emitting a plurality of light pulses at a pulse frequency between about 1 MHz and about 100 MHz. In some examples, the pulse frequency of the light pulses may correspond to an acoustic resonant frequency of the ultrasonic sensor array and the substrate. For example, a set of four or more light pulses may be emitted from the light source system 204 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 204. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 206 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 206 also may include (and/or be configured for communication with) one or more memory devices, such as one or more random access memory (RAM) devices, read-only memory (ROM) devices, etc. Accordingly, the apparatus 200 may have a memory system that includes one or more memory devices, though the memory system is not shown in FIG. 2. The control system 206 may be capable of receiving and processing data from the ultrasonic sensor array 202, e.g., as described below. If the apparatus 200 includes an ultrasonic transmitter 208, the control system 206 may be capable of controlling the ultrasonic transmitter 208, e.g., as disclosed elsewhere herein. In some implementations, functionality of the control system 206 may be partitioned between one or more controllers or processors, such as a dedicated sensor controller and an applications processor of a mobile device.

Although not shown in FIG. 2, some implementations of the apparatus 200 may include an interface system. In some examples, the interface system may include a wireless interface system. In some implementations, the interface system may include a user interface system, one or more network interfaces, one or more interfaces between the control system 206 and a memory system and/or one or more interfaces between the control system 206 and one or more external device interfaces (e.g., ports or applications processors).

The apparatus 200 may be used in a variety of different contexts, many examples of which are disclosed herein. For example, in some implementations a mobile device may include the apparatus 200. In some implementations, a wearable device may include the apparatus 200. The wearable device may, for example, be a bracelet, an armband, a wristband, a ring, a headband or a patch.

Figure 3:
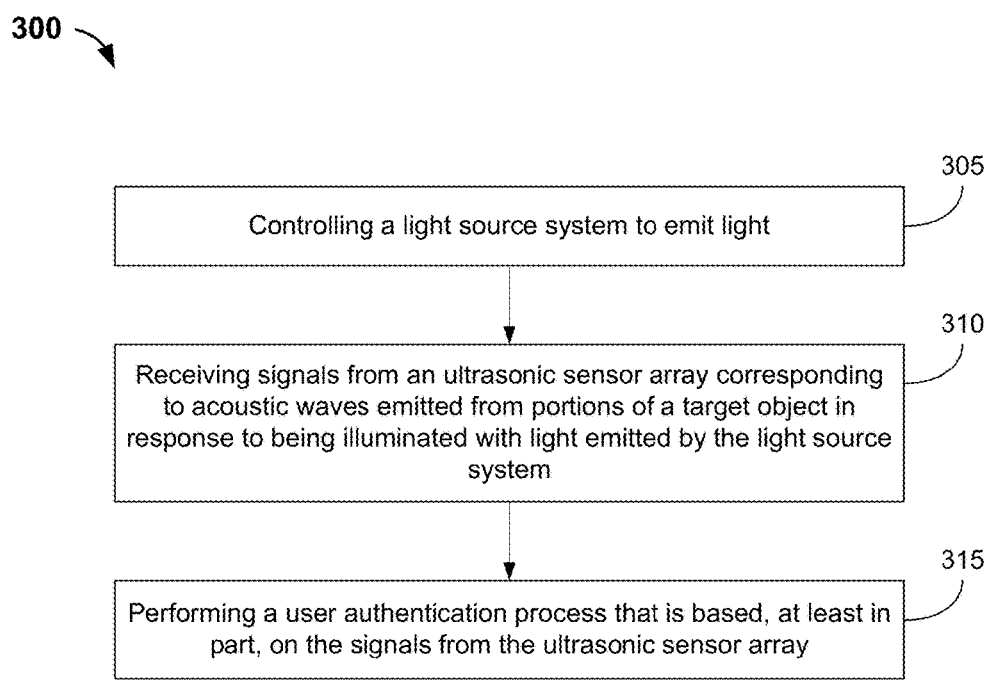
FIG. 3 is a flow diagram that provides examples of biometric system operations.

FIG. 3 is a flow diagram that provides examples of biometric system operations. The blocks of FIG. 3 (and those of other flow diagrams provided herein) may, for example, be performed by the apparatus 200 of FIG. 2 or by a similar apparatus. As with other methods disclosed herein, the method outlined in FIG. 3 may include more or fewer blocks than indicated. Moreover, the blocks of methods disclosed herein are not necessarily performed in the order indicated.

Here, block 305 involves controlling a light source system to emit light. In some implementations, the control system 206 of the apparatus 200 may control the light source system 204 to emit light. According to some such implementations, the control system may be capable of selecting one or more wavelengths of the light emitted by the light source system. In some implementations, the control system may be capable of selecting a light intensity associated with each selected wavelength. For example, the control system may be capable of selecting the one or more wavelengths of light and light intensities associated with each selected wavelength to generate acoustic wave emissions from one or more portions of the target object. In some examples, the control system may be capable of selecting the one or more wavelengths of light to evaluate a one or more characteristics of the target object, e.g., to evaluate blood oxygen levels. Some examples are described below. In some examples, block 305 may involve controlling a light source system to emit light that is transmitted through a substrate and/or other layers of an apparatus such as the apparatus 200.

According to this implementation, block 310 involves receiving signals from an ultrasonic sensor array corresponding to acoustic waves emitted from portions of a target object in response to being illuminated with light emitted by the light source system. In some instances the target object may be positioned on a surface of the ultrasonic sensor array or positioned on a surface of a platen that is acoustically coupled to the ultrasonic sensor array. The ultrasonic sensor array may, in some implementations, be the ultrasonic sensor array 202 that is shown in FIG. 2 and described above. One or more coatings or acoustic matching layers may be included with the platen.

In some examples the target object may be a finger, as shown above in FIG. 1 and as described below with reference to FIG. 4. However, in other examples the target object may be another body part, such as a palm, a wrist, an arm, a leg, a torso, a head, etc. In some examples the target object may be a finger-like object that is being used in an attempt to spoof the apparatus 200, or another such apparatus, into erroneously authenticating the finger-like object. For example, the finger-like object may include silicone rubber, polyvinyl acetate (white glue), gelatin, glycerin, etc., with a fingerprint pattern formed on an outside surface.

In some examples, the control system may be capable of selecting an acquisition time delay to receive acoustic wave emissions at a corresponding distance from the ultrasonic sensor array. The corresponding distance may correspond to a depth within the target object. According to some examples, the control system may be capable of receiving an acquisition time delay via a user interface, from a data structure stored in memory, etc.

In some implementations, the control system may be capable of acquiring first ultrasonic image data from acoustic wave emissions that are received by an ultrasonic sensor array during a first acquisition time window that is initiated at an end time of a first acquisition time delay. According to some examples, the control system may be capable of controlling a display to depict a two-dimensional (2-D) image that corresponds with the first ultrasonic image data. In some instances, the control system may be capable of acquiring second through $N^{th}$ ultrasonic image data during second through $N^{th}$ acquisition time windows after second through $N^{th}$ acquisition time delays. Each of the second through $N^{th}$ acquisition time delays may correspond to second through $N^{th}$ depths inside the target object. According to some examples, the control system may be capable of controlling a display to depict a reconstructed three-dimensional (3-D) image that corresponds with at least a subset of the first through $N^{th}$ ultrasonic image data. Some examples are described below.

In this instance, block 315 involves performing a user authentication process that is based, at least in part, on the signals from the ultrasonic sensor array. Accordingly, in some examples, the user authentication process may involve obtaining ultrasonic image data via illumination of the target object with light emitted from the light source system. In some such examples, the ultrasonic image data obtained via illumination of the target object may include image data corresponding to one or more sub-epidermal features, such as vascular image data.

According to some such implementations, the user authentication process also may involve obtaining ultrasonic image data via insonification of the target object with ultrasonic waves from an ultrasonic transmitter, such as the ultrasonic transmitter 208 shown in FIG. 2. In some such examples, the ultrasonic image data obtained via insonification of the target object may include fingerprint image data. However, in some implementations the ultrasonic image data obtained via illumination of the target object and the ultrasonic image data obtained via insonification of the target object may both be acquired primarily from the same depth inside the target object. In some examples, both the ultrasonic image data obtained via illumination of the target object and the ultrasonic image data obtained via insonification of the target object may be acquired from the same plurality of sensor pixels within an ultrasonic sensor array.

The user authentication process may involve comparing "attribute information" obtained from received image data, based on the signals from the ultrasonic sensor array, with stored attribute information obtained from image data that has previously been received from an authorized user during, for example, an enrollment process. In some examples, the attribute information obtained from received image data and the stored attribute information include attribute information regarding subdermal features. According to some such examples, the attribute information may include information regarding subdermal features, such as information regarding features of the dermis, features of the subcutis, blood vessel features, lymph vessel features, sweat gland features, hair follicle features, hair papilla features and/or fat lobule features.

Alternatively, or additionally, in some implementations the attribute information obtained from the received image data and the stored attribute information may include information regarding bone tissue features, muscle tissue features and/or epidermal tissue features. For example, according to some implementations, the user authentication process may involve controlling the ultrasonic transmitter to obtain fingerprint image data via the ultrasonic sensor array. In such examples, the authentication process may involve evaluating attribute information obtained from the fingerprint image data.

The attribute information obtained from the received image data and the stored attribute information that are compared during an authentication process may include biometric template data corresponding to the received image data and biometric template data corresponding to the stored image data. One well-known type of biometric template data is fingerprint template data, which may indicate types and locations of fingerprint minutia. A user authentication process based on attributes of fingerprint image data may involve comparing received and stored fingerprint template data. Such a process may or may not involve directly comparing received and stored fingerprint image data.

Similarly, biometric template data corresponding to subdermal features may include information regarding the attributes of blood vessels, such as information regarding the types and locations of blood vessel features, such as blood vessel size, blood vessel orientation, the locations of blood vessel branch points, etc. Alternatively, or additionally, biometric template data corresponding to subdermal features may include attribute information regarding the types (e.g., the sizes, shapes, orientations, etc.) and locations of features of the dermis, features of the subcutis, lymph vessel features, sweat gland features, hair follicle features, hair papilla features and/or fat lobule features.

Many spoofing techniques are based on forming fingerprint-like features on an object, which may be a finger-like object. However, making a finger-like object with detailed subdermal features, muscle tissue features and/or bone tissue features would be challenging and expensive. Making such features accurately correspond with those of an authorized user would be even more challenging. Because some disclosed implementations involve obtaining attribute information that is based on sub-epidermal features, muscle tissue features and/or bone tissue features, some such implementations may provide more reliable authentication and may be capable of providing determinations of "liveness." Some implementations described below, such as those capable of determining changes in blood oxygen and/or blood glucose levels, may provide enhanced liveness determinations.

Figure 4:
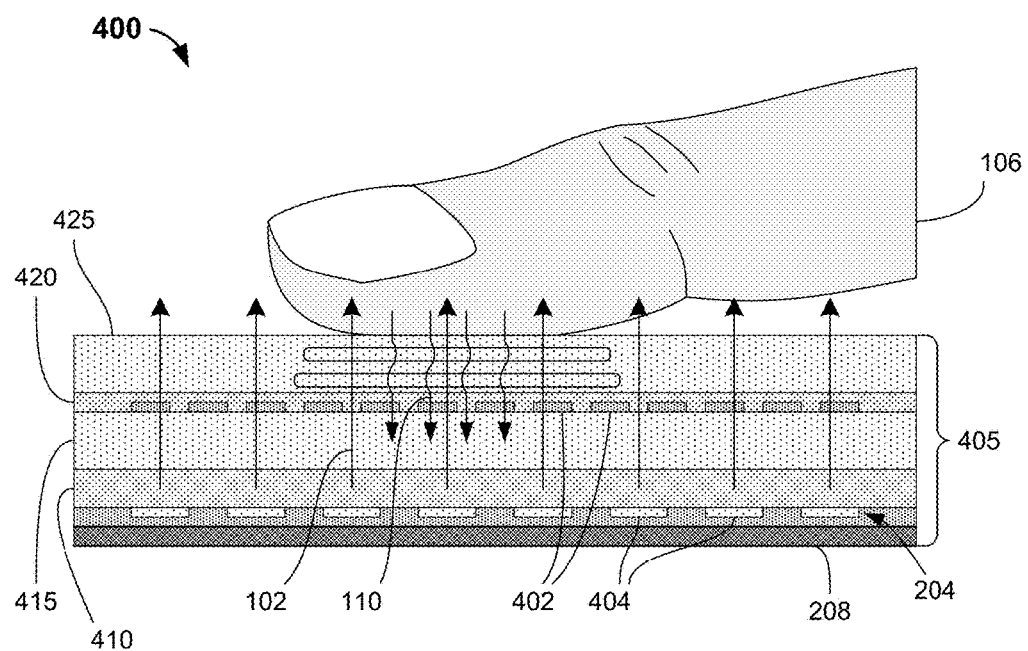
FIG. 4 shows an example of a cross-sectional view of an apparatus capable of performing the method of FIG. 3.

FIG. 4 shows an example of a cross-sectional view of an apparatus capable of performing the method of FIG. 3. The apparatus 400 is an example of a device that may be included in a biometric system such as those disclosed herein. Here, the apparatus 400 is an implementation of the apparatus 200 that is described above with reference to FIG. 2. As with other implementations shown and described herein, the types of elements, the arrangement of the elements and the dimensions of the elements illustrated in FIG. 4 are merely shown by way of example.

FIG. 4 shows an example of a target object being illuminated by incident light and subsequently emitting acoustic waves. In this example, the apparatus 400 includes a light source system 204, which may include an array of light-emitting diodes and/or an array of laser diodes. In some implementations, the light source system 204 may be capable of emitting various wavelengths of light, which may be selectable to trigger acoustic wave emissions primarily from a particular type of material. In some instances, the incident light wavelength, wavelengths and/or wavelength range(s) may be selected to trigger acoustic wave emissions primarily from a particular type of material, such as blood, blood vessels, other soft tissue, or bones. To achieve sufficient image contrast, light sources 404 of the light source system 204 may need to have a higher intensity and optical power output than light sources generally used to illuminate displays. In some implementations, light sources with light output of 1-100 millijoules or more per pulse, with pulse widths of 100 nanoseconds or less, may be suitable. In some implementations, light from an electronic flash unit such as that associated with a mobile device may be suitable. In some implementations, the pulse width of the emitted light may be between about 10 nanoseconds and about 500 nanoseconds or more.

In this example, incident light 102 has been transmitted from the light sources 404 of the light system 204 through a sensor stack 405 and into an overlying finger 106. The various layers of the sensor stack 405 may include one or more substrates of glass or other material such as plastic or sapphire that is substantially transparent to the light emitted by the light source system 204. In this example, the sensor stack 405 includes a substrate 410 to which the light source system 204 is coupled, which may be a backlight of a display according to some implementations. In alternative implementations, the light source system 204 may be coupled to a front light. Accordingly, in some implementations the light source system 204 may be configured for illuminating a display and the target object.

In this implementation, the substrate 410 is coupled to a thin-film transistor (TFT) substrate 415 for the ultrasonic sensor array 202. According to this example, a piezoelectric receiver layer 420 overlies the sensor pixels 402 of the ultrasonic sensor array 202 and a platen 425 overlies the piezoelectric receiver layer 420. Accordingly, in this example the apparatus 400 is capable of transmitting the incident light 102 through one or more substrates of the sensor stack 405 that include the ultrasonic sensor array 202 with substrate 415 and the platen 425 that may also be viewed as a substrate. In some implementations, sensor pixels 402 of the ultrasonic sensor array 202 may be transparent, partially transparent or substantially transparent, such that the apparatus 400 may be capable of transmitting the incident light 102 through elements of the ultrasonic sensor array 202. In some implementations, the ultrasonic sensor array 202 and associated circuitry may be formed on or in a glass, plastic or silicon substrate.

In this example, the portion of the apparatus 400 that is shown in FIG. 4 includes an ultrasonic sensor array 202 that is capable of functioning as an ultrasonic receiver. According to some implementations, the apparatus 400 may include an ultrasonic transmitter 208. The ultrasonic transmitter 208 may or may not be part of the ultrasonic sensor array 202, depending on the particular implementation. In some examples, the ultrasonic sensor array 202 may include PMUT or CMUT elements that are capable of transmitting and receiving ultrasonic waves, and the piezoelectric receiver layer 420 may be replaced with an acoustic coupling layer. In some examples, the ultrasonic sensor array 202 may include an array of pixel input electrodes and sensor pixels formed in part from TFT circuitry, an overlying piezoelectric receiver layer 420 of piezoelectric material such as PVDF or PVDF-TrFE, and an upper electrode layer positioned on the piezoelectric receiver layer sometimes referred to as a receiver bias electrode. In the example shown in FIG. 4, at least a portion of the apparatus 400 includes an ultrasonic transmitter 208 that can function as a plane-wave ultrasonic transmitter. The ultrasonic transmitter 208 may include a piezoelectric transmitter layer with transmitter excitation electrodes disposed on each side of the piezoelectric transmitter layer.

Here, the incident light 102 causes optical excitation within the finger 106 and resultant acoustic wave generation. In this example, the generated acoustic waves 110 include ultrasonic waves. Acoustic emissions generated by the absorption of incident light may be detected by the ultrasonic sensor array 202. A high signal-to-noise ratio may be obtained because the resulting ultrasonic waves are caused by optical stimulation instead of by reflection of transmitted ultrasonic waves.

Figure 5:
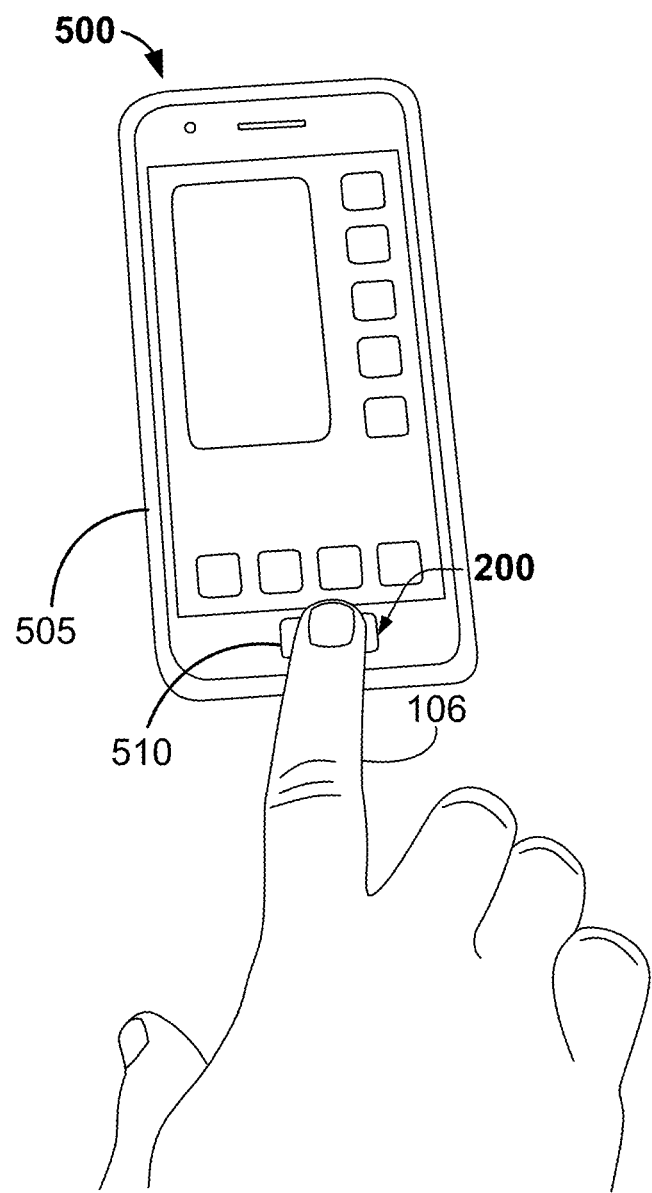
FIG. 5 shows an example of a mobile device that includes a biometric system as disclosed herein.

FIG. 5 shows an example of a mobile device that includes a biometric system as disclosed herein. In this example, the mobile device 500 is a smart phone. However, in alternative examples the mobile device 500 may another type of mobile device, such as a mobile health device, a wearable device, a tablet, etc.

In this example, the mobile device 500 includes an instance of the apparatus 200 that is described above with reference to FIG. 2. In this example, the apparatus 200 is disposed, at least in part, within the mobile device enclosure 505. According to this example, at least a portion of the apparatus 200 is located in the portion of the mobile device 500 that is shown being touched by the finger 106, which corresponds to the location of button 510. Accordingly, the button 510 may be an ultrasonic button. In some implementations, the button 510 may serve as a home button. In some implementations, the button 510 may serve as an ultrasonic authenticating button, with the ability to turn on or otherwise wake up the mobile device 500 when touched or pressed and/or to authenticate or otherwise validate a user when applications running on the mobile device (such as a wake-up function) warrant such a function. Light sources for photoacoustic imaging may be included within the button 510.

In this implementation, the mobile device 500 may be capable of performing a user authentication process. For example, a control system of the mobile device 500 may be capable of comparing attribute information obtained from image data received via an ultrasonic sensor array of the apparatus 200 with stored attribute information obtained from image data that has previously been received from an authorized user. In some examples, the attribute information obtained from the received image data and the stored attribute information may include attribute information corresponding to at least one of sub-epidermal features, muscle tissue features or bone tissue features.

According to some implementations, the attribute information obtained from the received image data and the stored attribute information may include information regarding fingerprint minutia. In some such implementations, the user authentication process may involve evaluating information regarding the fingerprint minutia as well as at least one other type of attribute information, such as attribute information corresponding to subdermal features. According to some such examples, the user authentication process may involve evaluating information regarding the fingerprint minutia as well as attribute information corresponding to vascular features. For example, attribute information obtained from a received image of blood vessels in the finger may be compared with a stored image of blood vessels in the authorized user's finger 106.

The apparatus 200 that is included in the mobile device 500 may or may not include an ultrasonic transmitter, depending on the particular implementation. However, in some examples, the user authentication process may involve obtaining ultrasonic image data via insonification of the target object with ultrasonic waves from an ultrasonic transmitter, as well as obtaining ultrasonic image data via illumination of the target object with light emitted from the light source system. According to some such examples, the ultrasonic image data obtained via insonification of the target object may include fingerprint image data and the ultrasonic image data obtained via illumination of the target object may include vascular image data.

Figure 6:
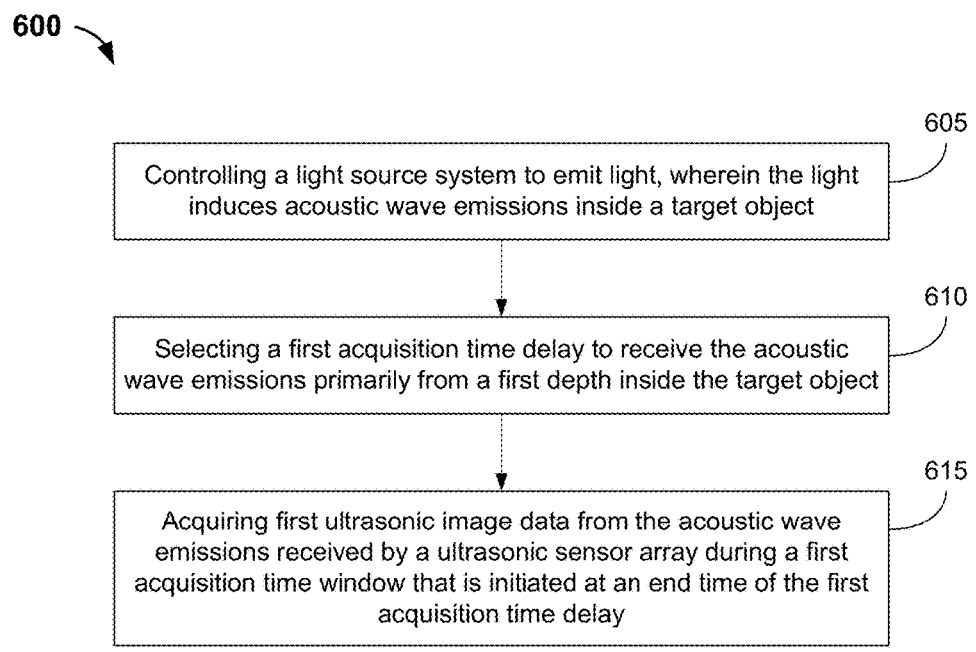
FIG. 6 is a flow diagram that provides further examples of biometric system operations.

FIG. 6 is a flow diagram that provides further examples of biometric system operations. The blocks of FIG. 6 (and those of other flow diagrams provided herein) may, for example, be performed by the apparatus 200 of FIG. 2 or by a similar apparatus. As with other methods disclosed herein, the method outlined in FIG. 6 may include more or fewer blocks than indicated. Moreover, the blocks of method 600, as well as other methods disclosed herein, are not necessarily performed in the order indicated.

Here, block 605 involves controlling a light source system to emit light. In this example, the light may induce acoustic wave emissions inside a target object in block 605. In some implementations, the control system 206 of the apparatus 200 may control the light source system 204 to emit light in block 605. According to some such implementations, the control system 206 may be capable of controlling the light source system 204 to emit at least one light pulse having a duration that is in the range of about 10 nanoseconds to about 500 nanoseconds or more. For example, the control system 206 may be capable of controlling the light source system 204 to emit at least one light pulse having a duration of approximately 10 nanoseconds, 20 nanoseconds, 30 nanoseconds, 40 nanoseconds, 50 nanoseconds, 60 nanoseconds, 70 nanoseconds, 80 nanoseconds, 90 nanoseconds, 100 nanoseconds, 120 nanoseconds, 140 nanoseconds, 150 nanoseconds, 160 nanoseconds, 180 nanoseconds, 200 nanoseconds, 300 nanoseconds, 400 nanoseconds, 500 nanoseconds, etc. In some such implementations, the control system 206 may be capable of controlling the light source system 204 to emit a plurality of light pulses at a frequency between about 1 MHz and about 100 MHz. In other words, regardless of the wavelength(s) of light being emitted by the light source system 204, the intervals between light pulses may correspond to a frequency between about 1 MHz and about 100 MHz or more. For example, the control system 206 may be capable of controlling the light source system 204 to emit a plurality of light pulses at a frequency of about 1 MHz, about 5 MHz, about 10 MHz, about 15 MHz, about 20 MHz, about 25 MHz, about 30 MHz, about 40 MHz, about 50 MHz, about 60 MHz, about 70 MHz, about 80 MHz, about 90 MHz, about 100 MHz, etc. In some examples, light emitted by the light source system 204 may be transmitted through an ultrasonic sensor array or through one or more substrates of a sensor stack that includes an ultrasonic sensor array.

According to this example, block 610 involves selecting a first acquisition time delay to receive the acoustic wave emissions primarily from a first depth inside the target object. In some such examples, the control system may be capable of selecting an acquisition time delay to receive acoustic wave emissions at a corresponding distance from the ultrasonic sensor array. The corresponding distance may correspond to a depth within the target object. According to some such examples, the acquisition time delay may be measured from a time that the light source system emits light. In some examples, the acquisition time delay may be in the range of about 10 nanoseconds to over about 2000 nanoseconds.

According to some examples, a control system (such as the control system 206) may be capable of selecting the first acquisition time delay. In some examples, the control system may be capable of selecting the acquisition time delay based, at least on part, on user input. For example, the control system may be capable of receiving an indication of target depth or a distance from a platen surface of the biometric system via a user interface. The control system may be capable of determining a corresponding acquisition time delay from a data structure stored in memory, by performing a calculation, etc. Accordingly, in some instances the control system's selection of an acquisition time delay may be according to user input and/or according to one or more acquisition time delays stored in memory.

In this implementation, block 615 involves acquiring first ultrasonic image data from the acoustic wave emissions received by an ultrasonic sensor array during a first acquisition time window that is initiated at an end time of the first acquisition time delay. Some implementations may involve controlling a display to depict a two-dimensional image that corresponds with the first ultrasonic image data. According to some implementations, the first ultrasonic image data may be acquired during the first acquisition time window from a peak detector circuit disposed in each of a plurality of sensor pixels within the ultrasonic sensor array. In some implementations, the peak detector circuitry may capture acoustic wave emissions or reflected ultrasonic wave signals during the acquisition time window. Some examples are described below with reference to FIG. 14.

In some examples, the first ultrasonic image data may include image data corresponding to one or more sub-epidermal features, such as vascular image data. According to some implementations, method 600 also may involve obtaining second ultrasonic image data via insonification of the target object with ultrasonic waves from an ultrasonic transmitter. In some such examples, the second ultrasonic image data may include fingerprint image data. However, in some implementations the first ultrasonic image data and the second ultrasonic image data may both be acquired primarily from the same depth inside the target object. In some examples, both the first ultrasonic image data and the second ultrasonic image data may be acquired from the same plurality of sensor pixels within an ultrasonic sensor array.

Figure 7:
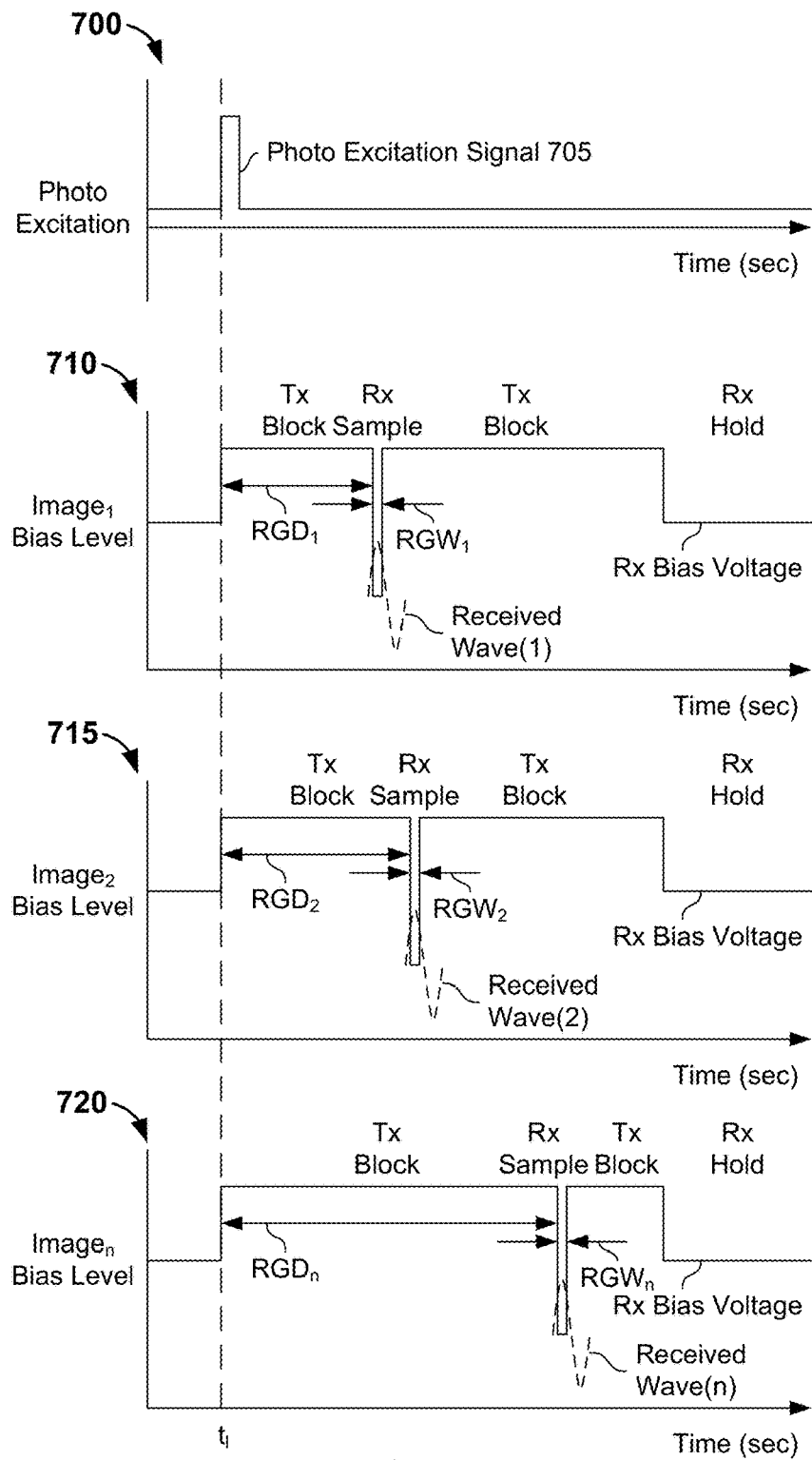
FIG. 7 shows examples of multiple acquisition time delays being selected to receive acoustic waves emitted from different depths.

FIG. 7 shows examples of multiple acquisition time delays being selected to receive acoustic waves emitted from different depths. In these examples, each of the acquisition time delays (which are labeled range-gate delays or RGDs in FIG. 7) is measured from the beginning time $t_1$ of the photo-excitation signal 705 shown in graph 700. The graph 710 depicts emitted acoustic waves (received wave (1) is one example) that may be received by an ultrasonic sensor array at an acquisition time delay $RGD_1$ and sampled during an acquisition time window (also known as a range-gate window or a range-gate width) of $RGW_1$. Such acoustic waves will generally be emitted from a relatively shallower portion of a target object proximate, or positioned upon, a platen of the biometric system.

Graph 715 depicts emitted acoustic waves (received wave (2) is one example) that are received by the ultrasonic sensor array at an acquisition time delay $RGD_2$ (with $RGD_2 > RGD_1$) and sampled during an acquisition time window of $RGW_2$. Such acoustic waves will generally be emitted from a relatively deeper portion of the target object. Graph 720 depicts emitted acoustic waves (received wave (n) is one example) that are received at an acquisition time delay $RGD_n$ (with $RGD_n > RGD_2 > RGD_1$) and sampled during an acquisition time window of $RGW_n$. Such acoustic waves will generally be emitted from a still deeper portion of the target object. Range-gate delays are typically integer multiples of a clock period. A clock frequency of 128 MHz, for example, has a clock period of 7.8125 nanoseconds, and RGDs may range from under 10 nanoseconds to over 2000 nanoseconds. Similarly, the range-gate widths may also be integer multiples of the clock period, but are often much shorter than the RGD (e.g. less than about 50 nanoseconds) to capture returning signals while retaining good axial resolution. In some implementations, the acquisition time window (e.g. RGW) may be between less than about 10 nanoseconds to about 200 nanoseconds or more. Note that while various image bias levels (e.g. Tx block, Rx sample and Rx hold that may be applied to an Rx bias electrode) may be in the single or low double-digit volt range, the return signals may have voltages in the tens or hundreds of millivolts.

Figure 8:
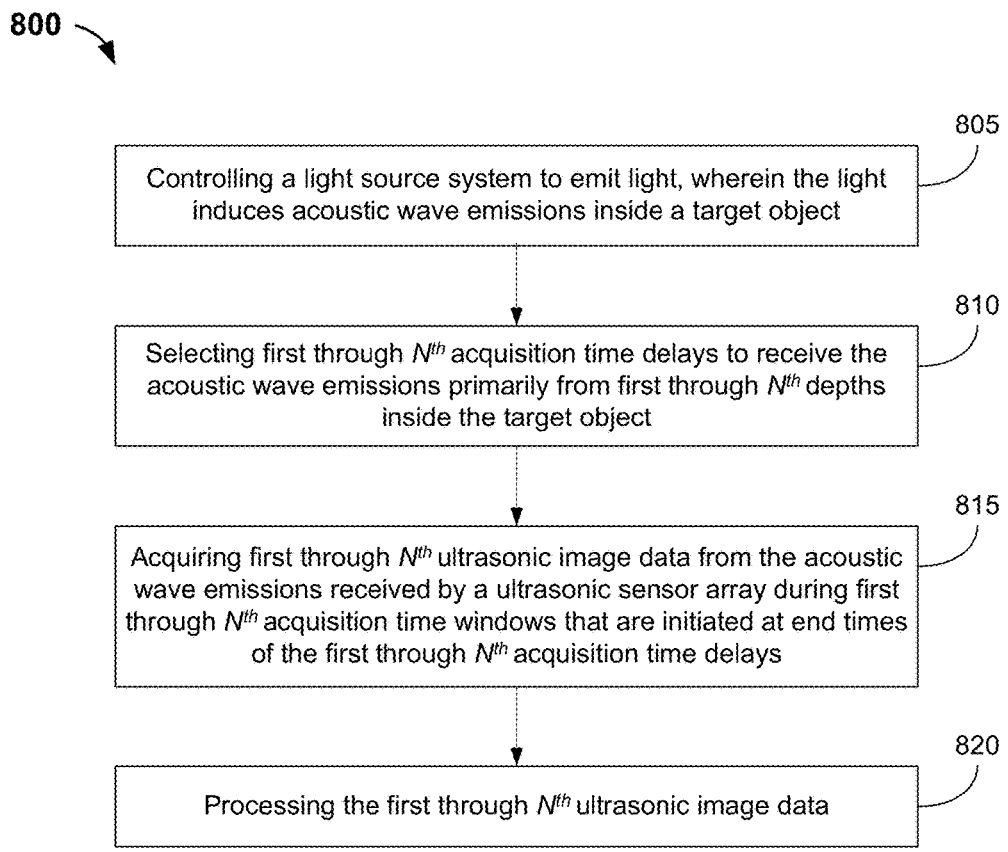
FIG. 8 is a flow diagram that provides additional examples of biometric system operations.

FIG. 8 is a flow diagram that provides additional examples of biometric system operations. The blocks of FIG. 8 (and those of other flow diagrams provided herein) may, for example, be performed by the apparatus 200 of FIG. 2 or by a similar apparatus. As with other methods disclosed herein, the method outlined in FIG. 8 may include more or fewer blocks than indicated. Moreover, the blocks of method 800, as well as other methods disclosed herein, are not necessarily performed in the order indicated.

Here, block 805 involves controlling a light source system to emit light. In this example, the light may induce acoustic wave emissions inside a target object in block 805. In some implementations, the control system 206 of the apparatus 200 may control the light source system 204 to emit light in block 805. According to some such implementations, the control system 206 may be capable of controlling the light source system 204 to emit at least one light pulse having a duration that is in the range of about 10 nanoseconds to about 500 nanoseconds. In some such implementations, the control system 206 may be capable of controlling the light source system 204 to emit a plurality of light pulses.

Figure 9:
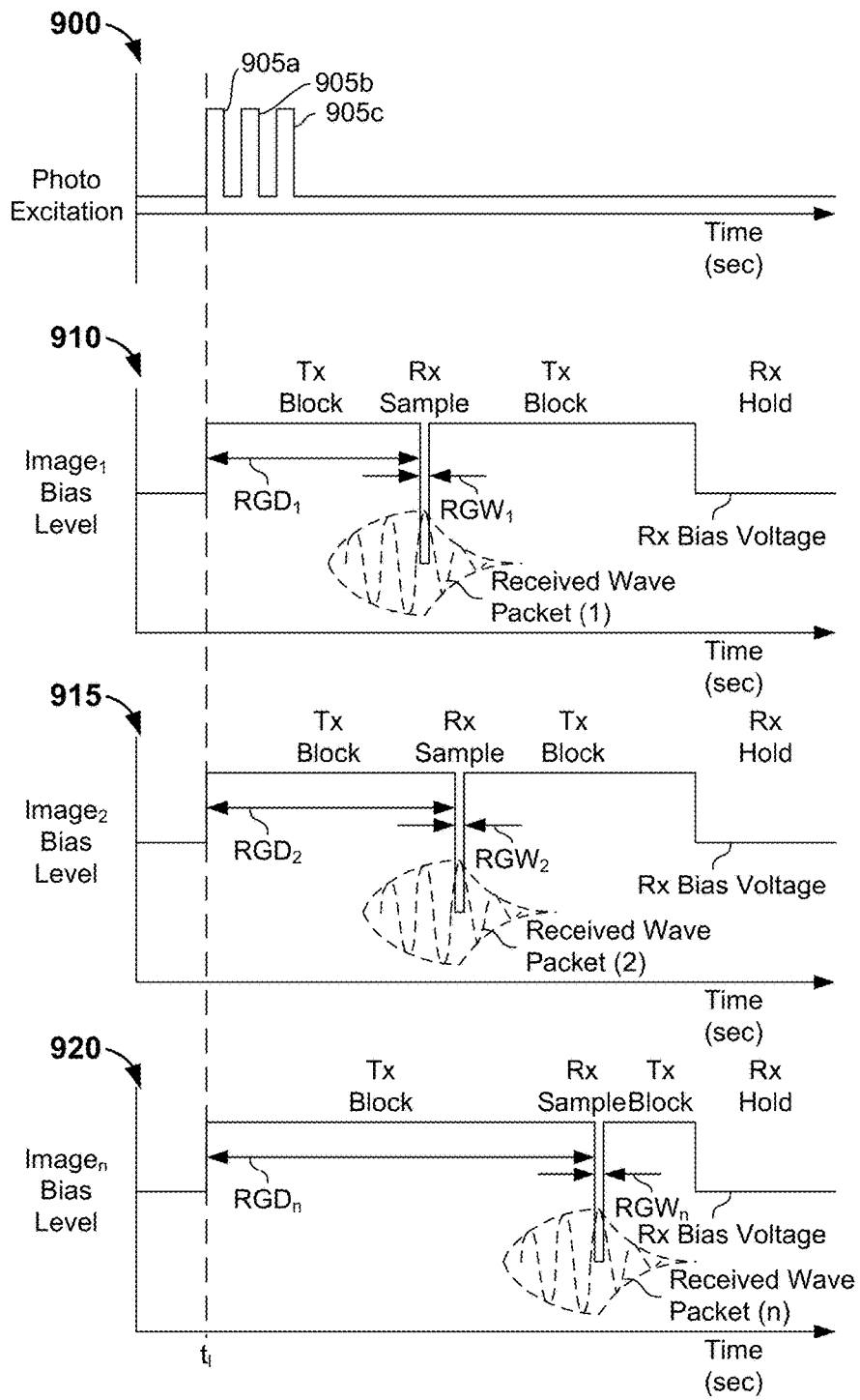
FIG. 9 shows examples of multiple acquisition time delays being selected to receive ultrasonic waves emitted from different depths, in response to a plurality of light pulses.

FIG. 9 shows examples of multiple acquisition time delays being selected to receive ultrasonic waves emitted from different depths, in response to a plurality of light pulses. In these examples, each of the acquisition time delays (which are labeled RGDs in FIG. 9) is measured from the beginning time $t_1$ of the photo-excitation signal 905a as shown in graph 900. Accordingly, the examples of FIG. 9 are similar to those of FIG. 7. However, in FIG. 9, the photo-excitation signal 905a is only the first of multiple photo-excitation signals. In this example, the multiple photo-excitation signals include the photo-excitation signals 905b and 905c, for a total of three photo-excitation signals. In other implementations, a control system may control a light source system to emit more or fewer photo-excitation signals. In some implementations, the control system may be capable of controlling the light source system to emit a plurality of light pulses at a frequency between about 1 MHz and about 100 MHz.

The graph 910 illustrates ultrasonic waves (received wave packet (1) is one example) that are received by an ultrasonic sensor array at an acquisition time delay $RGD_1$ and sampled during an acquisition time window of $RGW_1$. Such ultrasonic waves will generally be emitted from a relatively shallower portion of a target object proximate to, or positioned upon, a platen of the biometric system. By comparing received wave packet (1) with received wave (1) of FIG. 7, it may be seen that the received wave packet (1) has a relatively longer time duration and a higher amplitude buildup than that of received wave (1) of FIG. 7. This longer time duration corresponds with the multiple photo-excitation signals in the examples shown in FIG. 9, as compared to the single photo-excitation signal in the examples shown in FIG. 7.

Graph 915 illustrates ultrasonic waves (received wave packet (2) is one example) that are received by the ultrasonic sensor array at an acquisition time delay $RGD_2$ (with $RGD_2 > RGD_1$) and sampled during an acquisition time window of $RGW_2$. Such ultrasonic waves will generally be emitted from a relatively deeper portion of the target object. Graph 920 illustrates ultrasonic waves (received wave packet (n) is one example) that are received at an acquisition time delay $RGD_n$ (with $RGD_n > RGD_2 > RGD_1$) and sampled during an acquisition time window of $RGW_n$. Such ultrasonic waves will generally be emitted from still deeper portions of the target object.

Returning to FIG. 8, in this example block 810 involves selecting first through $N^{th}$ acquisition time delays to receive the acoustic wave emissions primarily from first through $N^{th}$ depths inside the target object. In some such examples, the control system may be capable of selecting the first through $N^{th}$ acquisition time delays to receive acoustic wave emissions at corresponding first through $N^{th}$ distances from the ultrasonic sensor array. The corresponding distances may correspond to first through $N^{th}$ depths within the target object. According to some such examples, (e.g., as shown in FIGS. 7 and 9), the acquisition time delays may be measured from a time that the light source system emits light. In some examples, the first through $N^{th}$ acquisition time delays may be in the range of about 10 nanoseconds to over about 2000 nanoseconds.

According to some examples, a control system (such as the control system 206) may be capable of selecting the first through $N^{th}$ acquisition time delays. In some examples, the control system may be capable of receiving one or more of the first through $N^{th}$ acquisition time delays (or one or more indications of depths or distances that correspond to acquisition time delays) from a user interface, from a data structure stored in memory, or by calculation of one or more depth-to-time conversions. Accordingly, in some instances the control system's selection of the first through $N^{th}$ acquisition time delays may be according to user input, according to one or more acquisition time delays stored in memory and/or according to a calculation.

In this implementation, block 815 involves acquiring first through $N^{th}$ ultrasonic image data from the acoustic wave emissions received by an ultrasonic sensor array during first through $N^{th}$ acquisition time windows that are initiated at end times of the first through $N^{th}$ acquisition time delays. According to some implementations, the first through $N^{th}$ ultrasonic image data may be acquired during first through $N^{th}$ acquisition time windows from a peak detector circuit disposed in each of a plurality of sensor pixels within the ultrasonic sensor array.

In this example, block 820 involves processing the first through $N^{th}$ ultrasonic image data. According to some implementations block 820 may involve controlling a display to depict a two-dimensional image that corresponds with one of the first through $N^{th}$ ultrasonic image data. In some implementations, block 820 may involve controlling a display to depict a reconstructed three-dimensional (3-D) image that corresponds with at least a subset of the first through $N^{th}$ ultrasonic image data. Various examples are described below with reference to FIGS. 10A-10F.

Figure 10A:
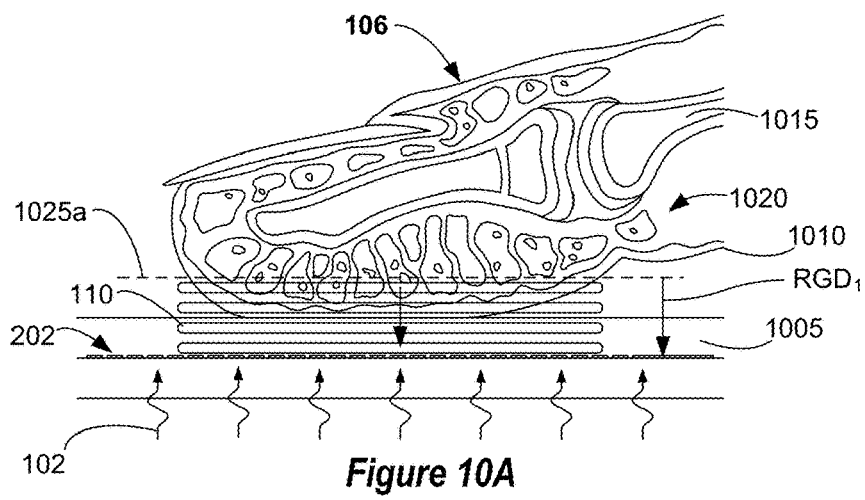
FIGS. 10A-10C are examples of cross-sectional views of a target object positioned on a platen of a biometric system such as those disclosed herein.
Figure 10B:
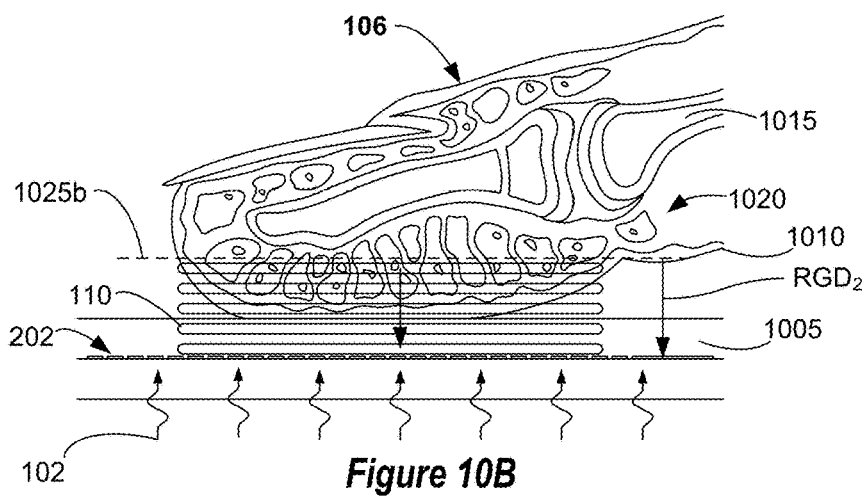
Figure 10C:
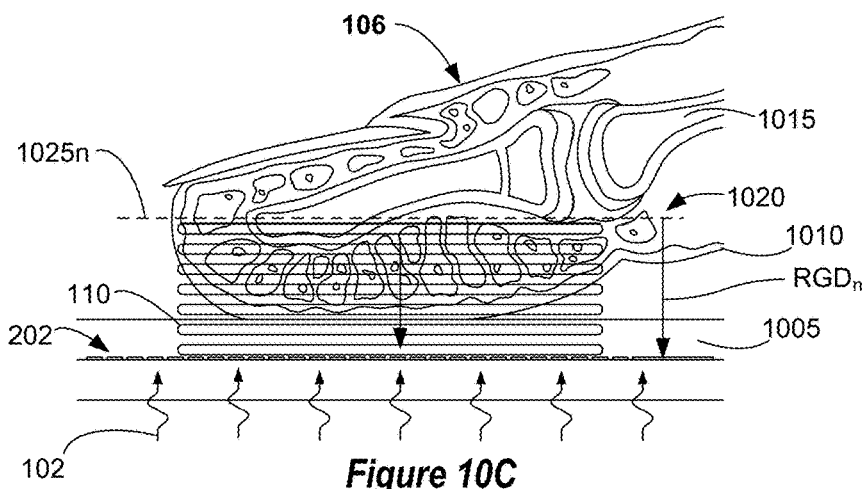

FIGS. 10A-10C are examples of cross-sectional views of a target object positioned on a platen of a biometric system such as those disclosed herein. In this example, the target object is a finger 106, which is positioned on an outer surface of a platen 1005. FIGS. 10A-10C show examples of tissues and structures of the finger 106, including the epidermis 1010, bone tissue 1015, blood vasculature 1020 and various sub-epidermal tissues. In this example, incident light 102 has been transmitted from a light source system (not shown) through the platen 1005 and into the finger 106. Here, the incident light 102 has caused optical excitation of the epidermis 1010 and blood vasculature 1020 and resultant generation of acoustic waves 110, which can be detected by the ultrasonic sensor array 202.

FIGS. 10A-10C indicate ultrasonic image data being acquired at three different range-gate delays ($RGD_1$, $RGD_2$ and $RGD_n$), which are also referred to herein as acquisition time delays, after the beginning of a time interval of photo excitation. The dashed horizontal lines 1025a, 1025b and 1025n in FIGS. 10A-10C indicate the depth of each corresponding image. In some examples the photo excitation may be a single pulse (e.g., as shown in FIG. 7), whereas in other examples the photo excitation may include multiple pulses (e.g., as shown in FIG. 9). FIG. 10D is a cross-sectional view of the target object illustrated in FIGS. 10A-10C showing the image planes 1025a, 1025b, . . . 1025n at varying depths through which image data has been acquired.

FIG. 10E shows a series of simplified two-dimensional images that correspond with ultrasonic image data acquired by the processes shown in FIGS. 10A-10C with reference to the image planes 1025a, 1025b and 1025n as shown in FIG. 10D. The two-dimensional images shown in FIG. 10E provide examples of two-dimensional images corresponding with ultrasonic image data that a control system could, in some implementations, cause a display device to display.

$Image_1$ of FIG. 10E corresponds with the ultrasonic image data acquired using $RGD_1$, which corresponds with the depth 1025a shown in FIGS. 10A and 10D. $Image_1$ includes a portion of the epidermis 1010 and blood vasculature 1020 and also indicates structures of the sub-epidermal tissues.

$Image_2$ corresponds with ultrasonic image data acquired using $RGD_2$, which corresponds with the depth 1025b shown in FIGS. 10B and 10D. $Image_2$ also includes a portion of the epidermis 1010, blood vasculature 1020 and indicates some additional structures of the sub-epidermal tissues.

$Image_n$ corresponds with ultrasonic image data acquired using $RGD_n$, which corresponds with the depth 1025n shown in FIGS. 10C and 10D. $Image_n$ includes a portion of the epidermis 1010, blood vasculature 1020, some additional structures of the sub-epidermal tissues and structures corresponding to bone tissue 1015. $Image_n$ also includes structures 1030 and 1032, which may correspond to bone tissue 1015 and/or to connective tissue near the bone tissue 1015, such as cartilage. However, it is not clear from $Image_1$, $Image_2$ or $Image_n$ what the structures of the blood vasculature 1020 and sub-epidermal tissues are or how they relate to one another.

These relationships may be more clearly seen the three-dimensional image shown in FIG. 10F. FIG. 10F shows a composite of $Image_1$, $Image_2$ and $Image_n$, as well as additional images corresponding to depths that are between depth 1025b and depth 1025n. A three-dimensional image may be made from a set of two-dimensional images according to various methods known by those of skill in the art, such as a MATLAB® reconstruction routine or other routine that enables reconstruction or estimations of three-dimensional structures from sets of two-dimensional layer data. These routines may use spline-fitting or other curve-fitting routines and statistical techniques with interpolation to provide approximate contours and shapes represented by the two-dimensional ultrasonic image data. As compared to the two-dimensional images shown in FIG. 10E, the three-dimensional image shown in FIG. 10F more clearly represents structures corresponding to bone tissue 1015 as well as sub-epidermal structures including blood vasculature 1020, revealing vein, artery and capillary structures and other vascular structures along with bone shape, size and features.

Figure 11:
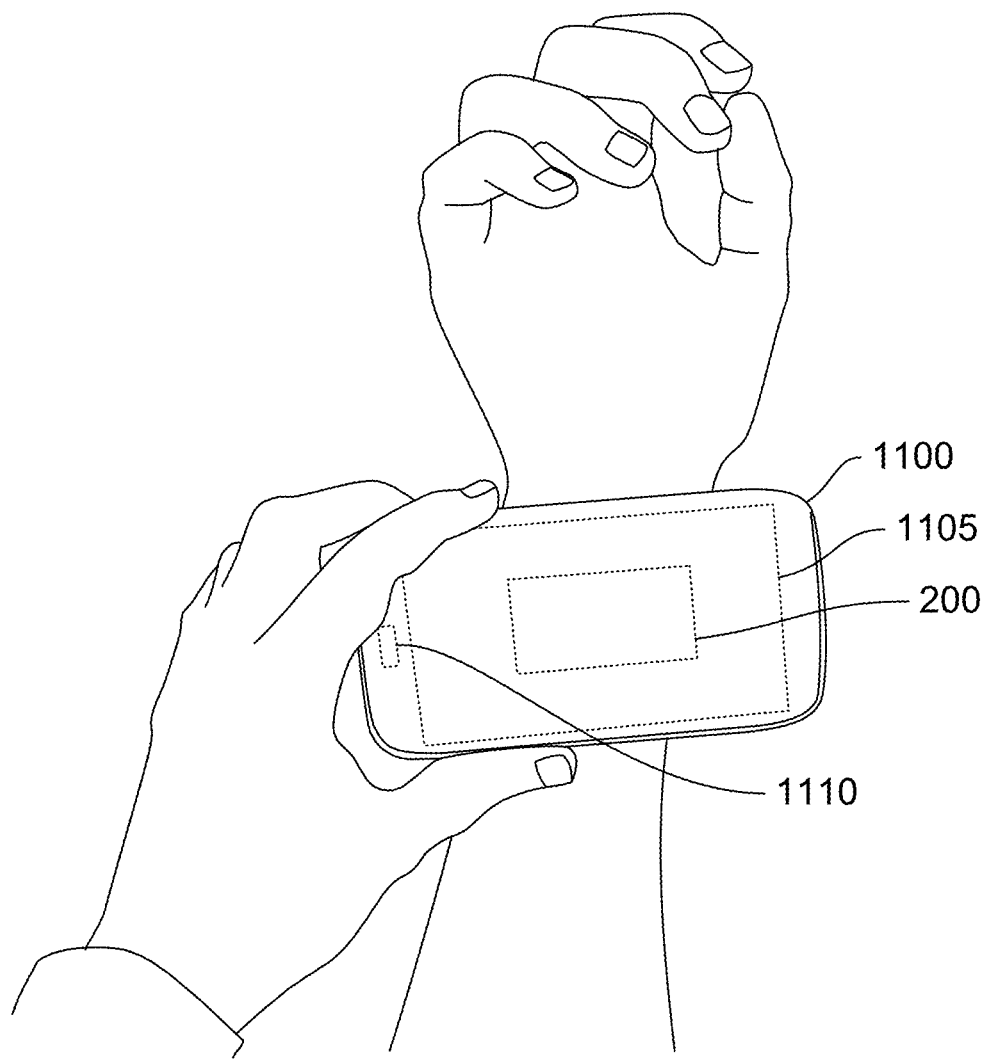
FIG. 11 shows an example of a mobile device that includes a biometric system capable of performing methods disclosed herein.

FIG. 11 shows an example of a mobile device that includes a biometric system capable of performing methods disclosed herein. A mobile device that includes such a biometric system may be capable of various types of mobile health monitoring, such as the imaging of blood vessel patterns, the analysis of blood and tissue components, etc.

In this example, the mobile device 1100 includes an instance of the apparatus 200 that is capable of functioning as an in-display photoacoustic imager (PAI). The apparatus 200 may, for example, be capable of emitting light that induces acoustic wave emissions inside a target object and acquiring ultrasonic image data from acoustic wave emissions received by an ultrasonic sensor array. In some examples, the apparatus 200 may be capable of acquiring ultrasonic image data during one or more acquisition time windows that are initiated at the end time of one or more acquisition time delays.

According to some implementations, the mobile device 1100 may be capable of displaying two-dimensional and/or three-dimensional images on the display 1105 that correspond with ultrasonic image data obtained via the apparatus 200. In other implementations, the mobile device may transmit ultrasonic image data (and/or attributes obtained from ultrasonic image data) to another device for processing and/or display.

In some examples, a control system of the mobile device 1100 (which may include a control system of the apparatus 200) may be capable of selecting one or more wavelengths of the light emitted by the apparatus 200. In some examples, the control system may be capable of selecting one or more wavelengths of light to trigger acoustic wave emissions primarily from a particular type of material in the target object. According to some implementations, the control system may be capable of estimating a blood oxygen level and/or of estimating a blood glucose level. In some implementations, the control system may be capable of selecting one or more wavelengths of light according to user input. For example, the mobile device 1100 may allow a user or a specialized software application to enter values corresponding to one or more wavelengths of the light emitted by the apparatus 200. Alternatively, or additionally, the mobile device 1100 may allow a user to select a desired function (such as estimating a blood oxygen level) and may determine one or more corresponding wavelengths of light to be emitted by the apparatus 200. For example, in some implementations, a wavelength in the mid-infrared region of the electromagnetic spectrum may be selected and a set of ultrasonic image data may be acquired in the vicinity of blood inside a blood vessel within a target object such as a finger or wrist. A second wavelength in another portion of the infrared region (e.g. near IR region) or in a visible region such as a red wavelength may be selected and a second set of ultrasonic image data may be acquired in the same vicinity as the first ultrasonic image data. A comparison of the first and second sets of ultrasonic image data, in conjunction with image data from other wavelengths or combinations of wavelengths, may allow an estimation of the blood glucose levels and/or blood oxygen levels within the target object.

In some implementations, a light source system of the mobile device 1100 may include at least one backlight or front light configured for illuminating the display 1105 and a target object. For example, the light source system may include one or more laser diodes, semiconductor lasers or light-emitting diodes. In some examples, the light source system may include at least one infrared, optical, red, green, blue, white or ultraviolet light-emitting diode or at least one infrared, optical, red, green, blue or ultraviolet laser diode. According to some implementations, the control system may be capable of controlling the light source system to emit at least one light pulse having a duration that is in the range of about 10 nanoseconds to about 500 nanoseconds. In some instances, the control system may be capable of controlling the light source system to emit a plurality of light pulses at a frequency between about 1 MHz and about 100 MHz.

In this example, the mobile device 1100 may include an ultrasonic authenticating button 1110 that includes another instance of the apparatus 200 that is capable of performing a user authentication process. In some such examples, the ultrasonic authenticating button 1110 may include an ultrasonic transmitter. According to some examples, the user authentication process may involve obtaining ultrasonic image data via insonification of a target object with ultrasonic waves from an ultrasonic transmitter and obtaining ultrasonic image data via illumination of the target object with light emitted from the light source system. In some such implementations, the ultrasonic image data obtained via insonification of the target object may include fingerprint image data and the ultrasonic image data obtained via illumination of the target object may include image data corresponding to one or more sub-epidermal features, such as vascular image data.

In this implementation, both the display 1105 and the apparatus 200 are on the side of the mobile device that is facing a target object, which is a wrist in this example, which may be imaged via the apparatus 200. However, in alternative implementations, the apparatus 200 may be on the opposite side of the mobile device 1100. For example, the display 1105 may be on the front of the mobile device and the apparatus 200 may be on the back of the mobile device. According to some such implementations, the mobile device may be capable of displaying two-dimensional and/or three-dimensional images, analogous to those shown in FIGS. 10E and 10F, as the corresponding ultrasonic image data are being acquired.

In some implementations, a portion of a target object, such as a wrist or arm, may be scanned as the mobile device 1100 is moved. According to some such implementations, a control system of the mobile device 1100 may be capable of stitching together the scanned images to form a more complete and larger two-dimensional or three-dimensional image. In some examples, the control system may be capable of acquiring first and second ultrasonic image data at primarily a first depth inside a target object. The second ultrasonic image data may be acquired after the target object or the mobile device 1100 is repositioned. In some implementations, the second ultrasonic image data may be acquired after a period of time corresponding to a frame rate, such as a frame rate between about one frame per second and about thirty frames per second or more. According to some such examples, the control system may be capable of stitching together or otherwise assembling the first and second ultrasonic image data to form a composite ultrasonic image.

Figure 12:
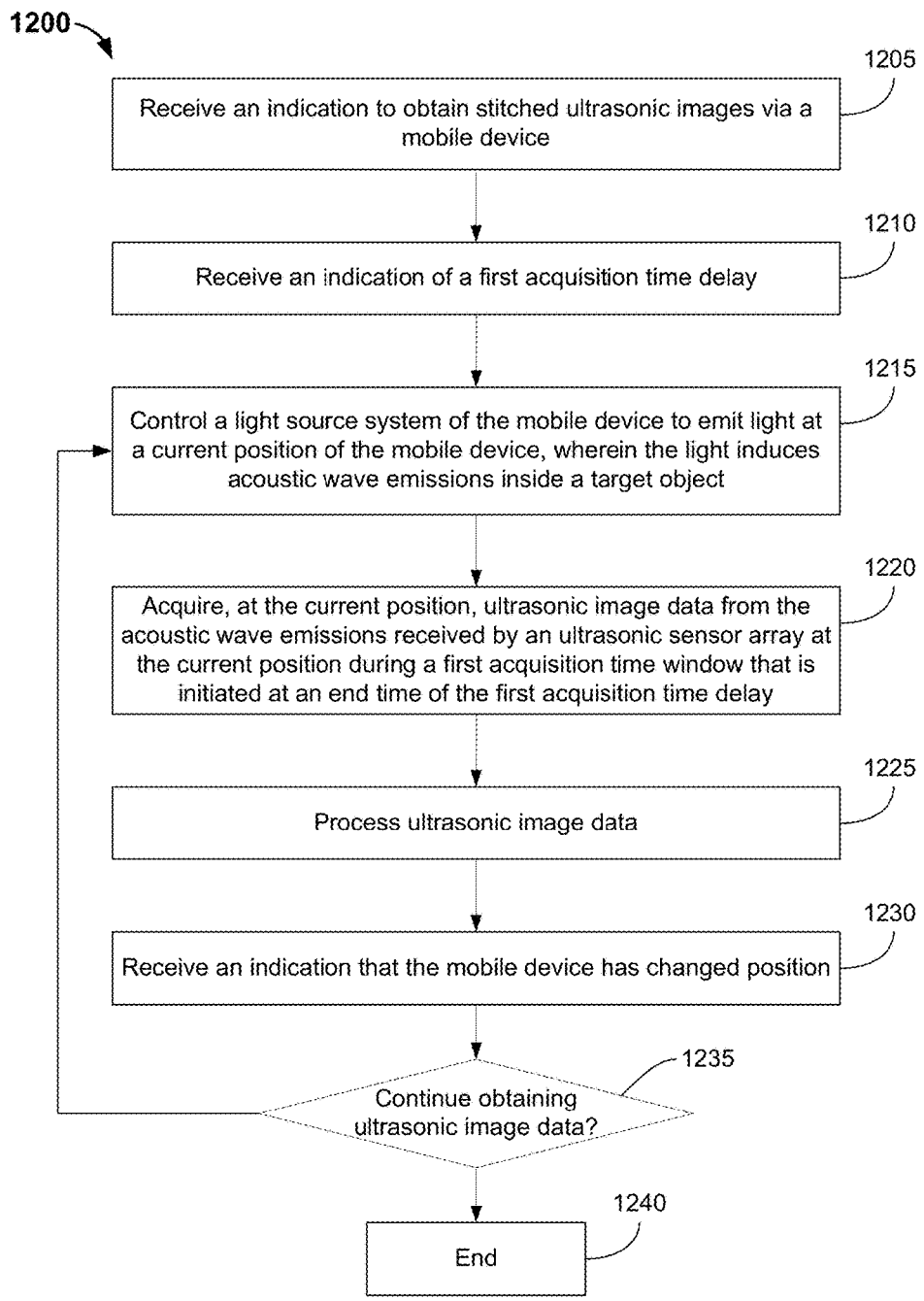
FIG. 12 is a flow diagram that provides an example of a method of stitching ultrasonic image data obtained via a mobile device such as that shown in FIG. 11.

FIG. 12 is a flow diagram that provides an example of a method of stitching ultrasonic image data obtained via a mobile device such as that shown in FIG. 11. As with other methods disclosed herein, the method outlined in FIG. 12 may include more or fewer blocks than indicated. Moreover, the blocks of method 1200 are not necessarily performed in the order indicated.

Here, block 1205 involves receiving an indication to obtain stitched ultrasonic images via a mobile device. In this example, block 1205 involves receiving an indication to obtain stitched two-dimensional ultrasonic images. In alternative examples, block 1205 may involve receiving an indication to obtain stitched three-dimensional ultrasonic images. For example, a software application running on a mobile device may recognize that a larger view of an area of interest within a target object is desired after receiving an answer to a prompt provided to a user, and provide an indication to stitch or otherwise assemble a collection of two-dimensional or three-dimensional images obtained as the mobile device is moved over and around the area of interest.

In this example, block 1210 involves receiving an indication of a first acquisition time delay. Block 1205 and/or block 1210 may, for example, involve receiving input from a user interface system, e.g., in response to user interaction with a graphical user interface via touch screen, in response to user interaction with a button, etc. In some implementations, the acquisition time delay may correspond with a distance from an ultrasonic sensor array of the mobile device and/or to a depth within a target object. Accordingly, the user input may correspond to time, distance, depth or another appropriate metric. In alternative examples wherein block 1205 involves receiving an indication to obtain stitched three-dimensional ultrasonic images, block 1210 may involve receiving an indication of first through $N^{th}$ acquisition time delays. According to some examples, a control system of the mobile device may receive one or more acquisition time delays from a user interface, from a data structure stored in memory, etc., in block 1210.

In this example, block 1215 involves controlling a light source system of the mobile device to emit light at a current position of the mobile device. In this example, the light induces acoustic wave emissions inside a target object. According to this implementation, block 1220 involves acquiring, at the current position, ultrasonic image data from the acoustic wave emissions. In this implementation, the acoustic wave emissions are received by an ultrasonic sensor array of the mobile at the current position of the mobile device during a first acquisition time window that is initiated at an end time of the first acquisition time delay. In alternative examples wherein block 1205 involves receiving an indication to obtain stitched three-dimensional ultrasonic images, block 1220 may involve acquiring, at the current position, ultrasonic image data during first through $N^{th}$ acquisition time windows after corresponding first through $N^{th}$ acquisition time delays.

In this implementation, block 1225 involves processing the acquired ultrasonic image data. In some examples, block 1225 may involve displaying the acquired ultrasonic image data. According to some implementations, block 1225 may involve identifying distinctive features of the acquired ultrasonic image data. Such distinctive features may be used for aligning the ultrasonic image data acquired in block 1220 with previously-acquired or subsequently-acquired ultrasonic image data from an overlapping area of the target object. Such distinctive features may be used during further processes of image stitching, e.g., as described below.

In this example, block 1230 involves receiving an indication that the mobile device has changed position. For example, block 1230 may involve receiving inertial sensor data from an inertial sensor system of the mobile device, such as sensor data from one or more accelerometers or angular rate sensors (e.g. gyroscopes) within the mobile device. Based on the inertial sensor data, a control system of the mobile device may determine that the mobile device has changed position. In some implementations, image data from a front-facing or rear-facing camera may be used to detect that the mobile device has changed position. In some implementations, a user may be prompted to provide an indication when the mobile device has changed positioned, for example, by pressing or otherwise touching an image-capture button.

In block 1235, it is determined whether to continue obtaining ultrasonic image data. In some instances, block 1235 may involve receiving an indication from a user interface system to stop obtaining ultrasonic image data. In some instances, block 1235 may involve receiving an indication as to whether a predetermined time interval for obtaining ultrasonic image data has elapsed.

If it is determined to continue obtaining ultrasonic image data in block 1235, in this example the process reverts to block 1215 and the light source system emits light at the current position of the mobile device. The process then continues to block 1220 and additional ultrasonic image data are acquired, at the current position, during the first acquisition time window that is initiated at the end time of the first acquisition time delay.

The process then continues to block 1225, in which at least the additional ultrasonic image data are processed. In some examples, at least the additional ultrasonic image data may be displayed. According to some implementations, block 1225 may involve identifying distinctive features of the additional ultrasonic image data. In some such implementations, the distinctive features may be used for aligning the additional ultrasonic image data acquired in block 1220 with previously-acquired or subsequently-acquired ultrasonic image data from an overlapping area of the target object.

Since at least two instances of ultrasonic image data will have been acquired after two iterations of blocks 1215 and 1220, block 1225 may involve a registration process for image stitching. In some implementations, the registration process may involve a search for image alignments that minimize the sum of absolute differences between values of overlapping image pixels. In some examples, the registration process may involve a random sample consensus (RANSAC) method. In some examples, block 1225 may involve an image alignment process. In some such implementations, block 1225 may involve a compositing process, during which images are aligned such that they appear as a single composite image. According to some implementations, block 1225 may involve an image blending process. For example, block 1225 may involve motion compensation, seam line adjustment to minimize the visibility of seams between adjacent images, etc.

In this implementation, method 1200 continues until it is determined in block 1235 not to continue obtaining ultrasonic image data, at which point the process ends. However, some implementations may involve additional operations after it is determined in block 1235 not to continue obtaining ultrasonic image data. In some such implementations, stitched ultrasonic image data may be displayed, stored in a memory and/or transmitted to another device.

Figure 13:
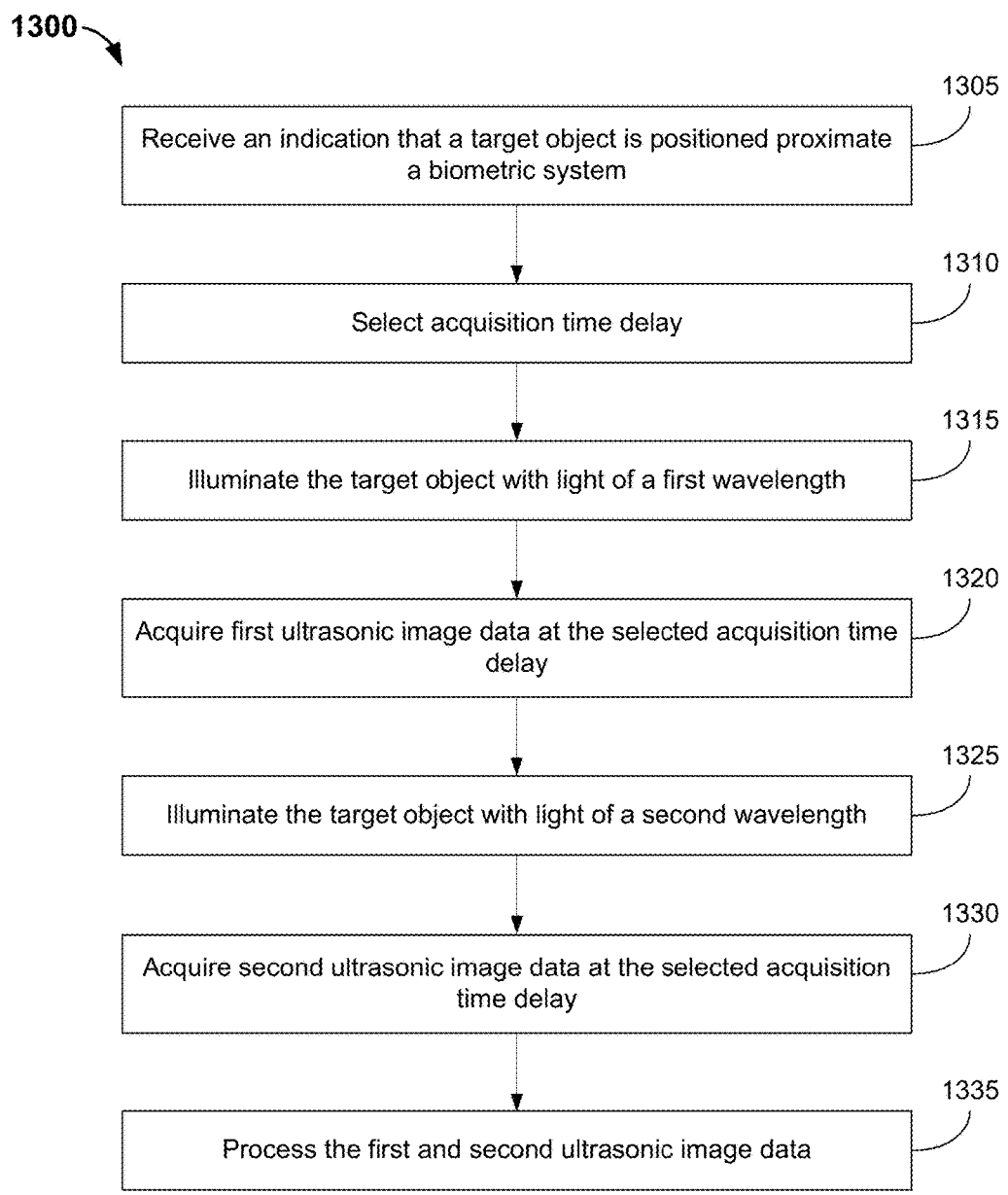
FIG. 13 is a flow diagram that shows blocks of a method of oxidized hemoglobin detection that may be performed with some disclosed biometric systems.

FIG. 13 is a flow diagram that shows blocks of a method of oxidized hemoglobin detection that may be performed with some disclosed biometric systems. As with other methods disclosed herein, the method outlined in FIG. 13 may include more or fewer blocks than indicated. Moreover, the blocks of method 1300 are not necessarily performed in the order indicated.

Here, block 1305 involves receiving an indication that a target object (such as a finger, palm or wrist) is positioned proximate a biometric system that includes an ultrasonic sensor array and a light source system. For example, block 1305 may involve receiving an indication that the target object is positioned on a platen of the biometric system. In some implementations, an application running on a mobile device having a biometric system with photoacoustic imaging capability may cue a user to touch or press a button to indicate when the target object is positioned on the platen. In some implementations, the biometric system may sense ultrasonically or capacitively when the target object is in contact with the platen surface and provide the indication accordingly.

In this implementation, block 1310 involves selecting an acquisition time delay. For example, block 1310 may involve selecting an acquisition time delay according to user input received from a user interface system. The acquisition time delay may correspond with a target of interest, such as blood in a blood vessel in this example. In some implementations, block 1310 also may involve selecting a first wavelength of light and a second wavelength of light and a light intensity associated with each selected wavelength for illuminating the target object. According to some implementations, block 1310 may involve selecting one or more wavelengths of light according to user input regarding a desired type of functionality, such as oxidized hemoglobin detection, estimating a blood glucose level, etc.

According to this example, block 1315 involves illuminating the target object with light of the first wavelength. For example, block 1315 may involve illuminating the target object with near-infrared light, which is strongly absorbed by oxygenated hemoglobin.

Here, block 1320 involves acquiring first ultrasonic image data at the selected acquisition time delay. In this example, the first ultrasonic image data corresponds to acoustic waves that were induced by illuminating the target object with light of the first wavelength, such as near-infrared light.

In this example, block 1325 involves illuminating the target object with light of the second wavelength. For example, instead of illuminating the target object with near-infrared light, block 1325 may involve illuminating the target object with a different wavelength of light, such as light in the visible range. Light in the visible range, such as red or green light, is not strongly absorbed by oxygenated hemoglobin, but instead tends to be transmitted.

According to this implementation, block 1330 involves acquiring second ultrasonic image data at the selected acquisition time delay. In this example, the second ultrasonic image data correspond to acoustic waves that were induced by illuminating the target object with light of the second wavelength, such as red or green light. By comparing the first ultrasonic image data with the second ultrasonic image data, blood oxygen levels may be estimated. For example, with appropriate calibration coefficients, the signal levels from the first ultrasonic image data may be normalized by the signal levels from the second ultrasonic image data in a region of interest such as within a blood vessel and the ratio compared to a stored table of values that converts the normalized data into, for example, blood oxygen level as a percentage of oxygen saturation (e.g. $SO_2$), as a percentage of peripheral oxygen saturation (e.g. $SpO_2$) or as a percentage of arterial oxygen saturation (e.g. $SaO_2$).

Figure 14:
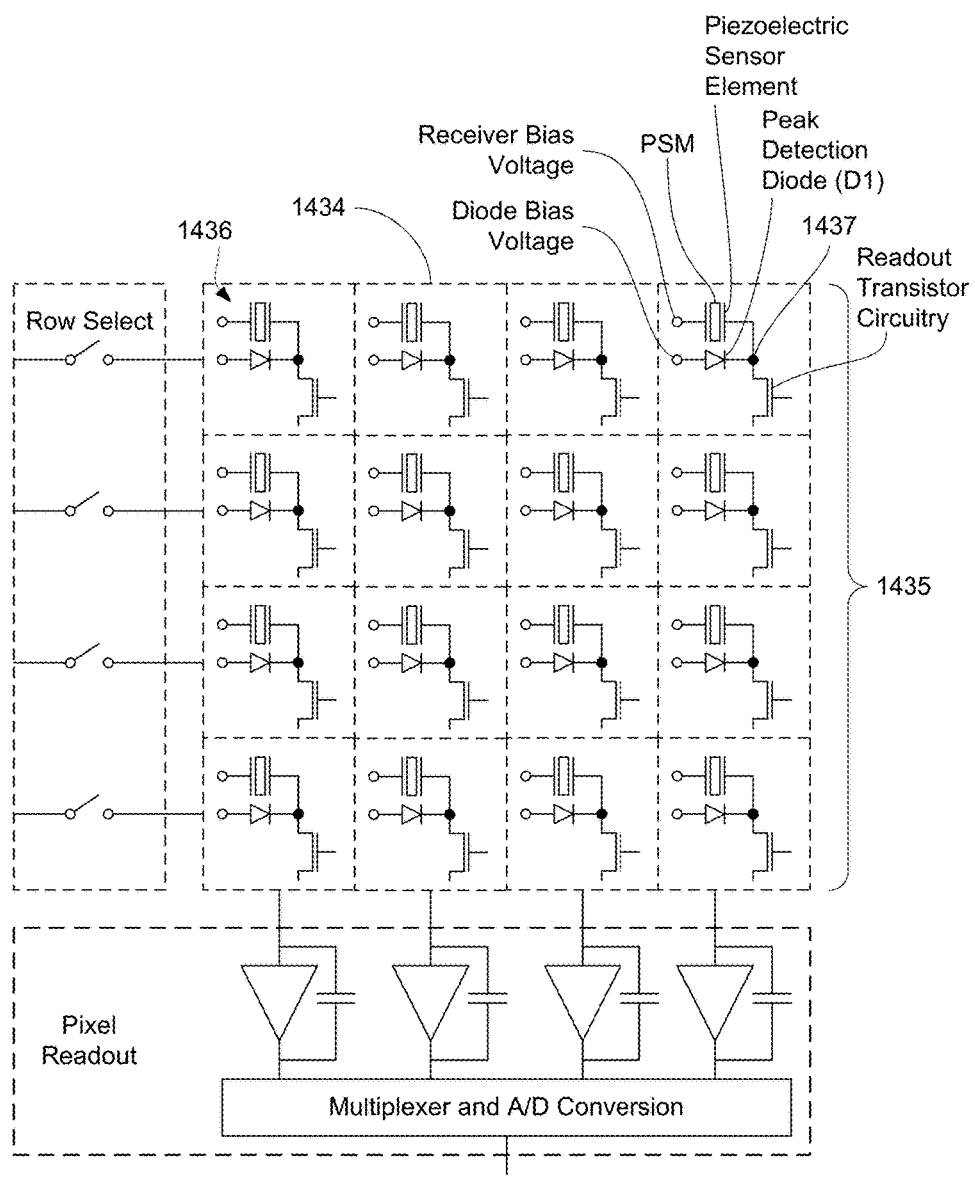
FIG. 14 representationally depicts aspects of a 4×4 pixel array of sensor pixels for an ultrasonic sensor system.

FIG. 14 representationally depicts aspects of a 4×4 pixel array 1435 of sensor pixels 1434 for an ultrasonic sensor system. Each pixel 1434 may be, for example, associated with a local region of piezoelectric sensor material (PSM), a peak detection diode (D1) and a readout transistor (M3); many or all of these elements may be formed on or in a substrate to form the pixel circuit 1436. In practice, the local region of piezoelectric sensor material of each pixel 1434 may transduce received ultrasonic energy into electrical charges. The peak detection diode D1 may register the maximum amount of charge detected by the local region of piezoelectric sensor material PSM. Each row of the pixel array 1435 may then be scanned, e.g., through a row select mechanism, a gate driver, or a shift register, and the readout transistor M3 for each column may be triggered to allow the magnitude of the peak charge for each pixel 1434 to be read by additional circuitry, e.g., a multiplexer and an A/D converter. The pixel circuit 1436 may include one or more TFTs to allow gating, addressing, and resetting of the pixel 1434.

Each pixel circuit 1436 may provide information about a small portion of the object detected by the ultrasonic sensor system. While, for convenience of illustration, the example shown in FIG. 14 is of a relatively coarse resolution, ultrasonic sensors having a resolution on the order of 500 pixels per inch or higher may be configured with an appropriately scaled structure. The detection area of the ultrasonic sensor system may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the target object.

Figure 15A:
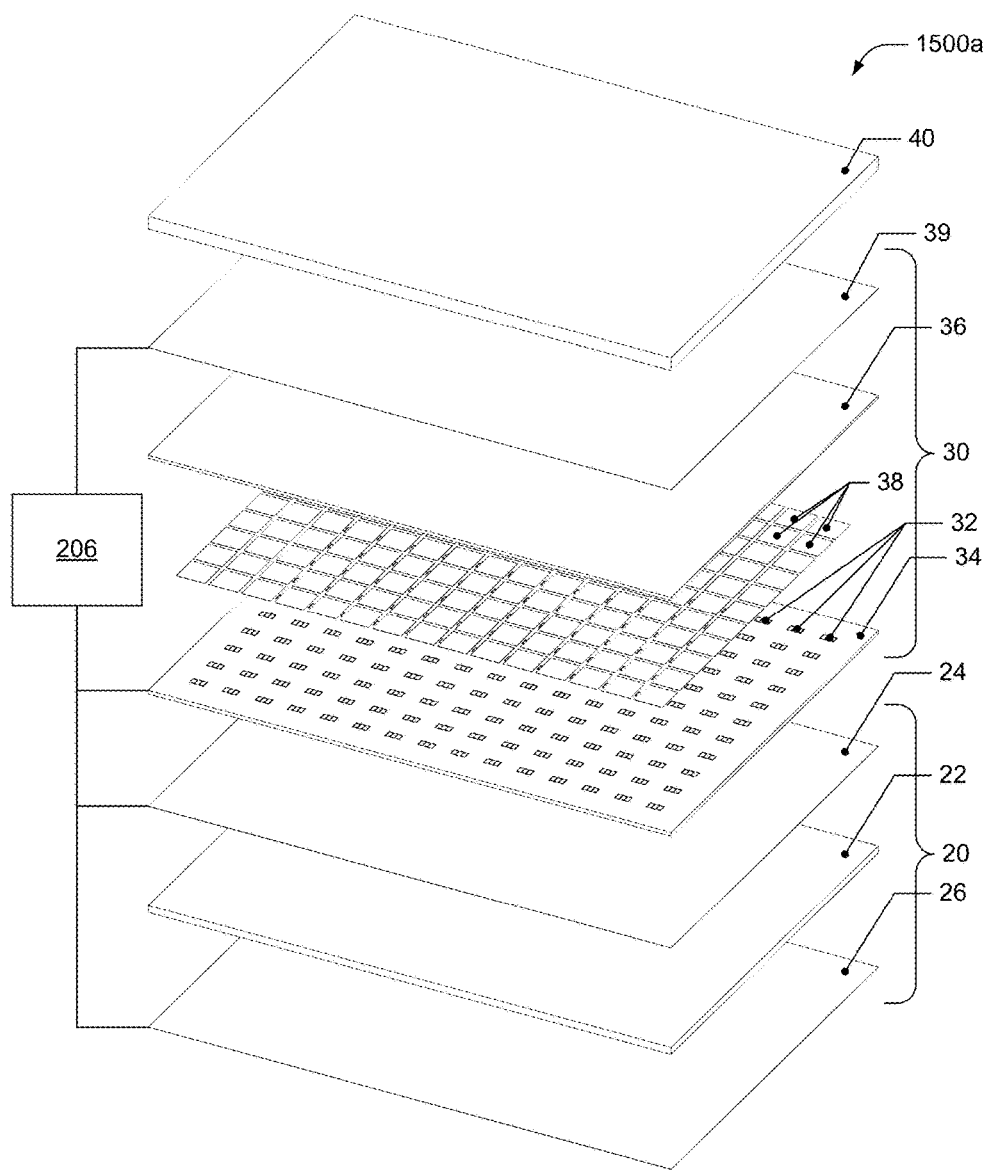
FIG. 15A shows an example of an exploded view of an ultrasonic sensor system.

FIG. 15A shows an example of an exploded view of an ultrasonic sensor system. In this example, the ultrasonic sensor system 1500a includes an ultrasonic transmitter 20 and an ultrasonic receiver 30 under a platen 40. According to some implementations, the ultrasonic receiver 30 may be an example of the ultrasonic sensor array 202 that is shown in FIG. 2 and described above. In some implementations, the ultrasonic transmitter 20 may be an example of the optional ultrasonic transmitter 208 that is shown in FIG. 2 and described above. The ultrasonic transmitter 20 may include a substantially planar piezoelectric transmitter layer 22 and may be capable of functioning as a plane wave generator. Ultrasonic waves may be generated by applying a voltage to the piezoelectric layer to expand or contract the layer, depending upon the signal applied, thereby generating a plane wave. In this example, the control system 206 may be capable of causing a voltage that may be applied to the planar piezoelectric transmitter layer 22 via a first transmitter electrode 24 and a second transmitter electrode 26. In this fashion, an ultrasonic wave may be made by changing the thickness of the layer via a piezoelectric effect. This ultrasonic wave may travel towards a finger (or other object to be detected), passing through the platen 40. A portion of the wave not absorbed or transmitted by the object to be detected may be reflected so as to pass back through the platen 40 and be received by the ultrasonic receiver 30. The first and second transmitter electrodes 24 and 26 may be metallized electrodes, for example, metal layers that coat opposing sides of the piezoelectric transmitter layer 22.

The ultrasonic receiver 30 may include an array of sensor pixel circuits 32 disposed on a substrate 34, which also may be referred to as a backplane, and a piezoelectric receiver layer 36. In some implementations, each sensor pixel circuit 32 may include one or more TFT elements, electrical interconnect traces and, in some implementations, one or more additional circuit elements such as diodes, capacitors, and the like. Each sensor pixel circuit 32 may be configured to convert an electric charge generated in the piezoelectric receiver layer 36 proximate to the pixel circuit into an electrical signal. Each sensor pixel circuit 32 may include a pixel input electrode 38 that electrically couples the piezoelectric receiver layer 36 to the sensor pixel circuit 32.

In the illustrated implementation, a receiver bias electrode 39 is disposed on a side of the piezoelectric receiver layer 36 proximal to platen 40. The receiver bias electrode 39 may be a metallized electrode and may be grounded or biased to control which signals may be passed to the array of sensor pixel circuits 32. Ultrasonic energy that is reflected from the exposed (top) surface of the platen 40 may be converted into localized electrical charges by the piezoelectric receiver layer 36. These localized charges may be collected by the pixel input electrodes 38 and passed on to the underlying sensor pixel circuits 32. The charges may be amplified or buffered by the sensor pixel circuits 32 and provided to the control system 206.

The control system 206 may be electrically connected (directly or indirectly) with the first transmitter electrode 24 and the second transmitter electrode 26, as well as with the receiver bias electrode 39 and the sensor pixel circuits 32 on the substrate 34. In some implementations, the control system 206 may operate substantially as described above. For example, the control system 206 may be capable of processing the amplified signals received from the sensor pixel circuits 32.

The control system 206 may be capable of controlling the ultrasonic transmitter 20 and/or the ultrasonic receiver 30 to obtain ultrasonic image data, e.g., by obtaining fingerprint images. Whether or not the ultrasonic sensor system 1500a includes an ultrasonic transmitter 20, the control system 206 may be capable of obtaining attribute information from the ultrasonic image data. In some examples, the control system 206 may be capable of controlling access to one or more devices based, at least in part, on the attribute information. The ultrasonic sensor system 1500a (or an associated device) may include a memory system that includes one or more memory devices. In some implementations, the control system 206 may include at least a portion of the memory system. The control system 206 may be capable of obtaining attribute information from ultrasonic image data and storing the attribute information in the memory system. In some implementations, the control system 206 may be capable of capturing a fingerprint image, obtaining attribute information from the fingerprint image and storing attribute information obtained from the fingerprint image (which may be referred to herein as fingerprint image information) in the memory system. According to some examples, the control system 206 may be capable of capturing a fingerprint image, obtaining attribute information from the fingerprint image and storing attribute information obtained from the fingerprint image even while maintaining the ultrasonic transmitter 20 in an "off" state.

In some implementations, the control system 206 may be capable of operating the ultrasonic sensor system 1500a in an ultrasonic imaging mode or a force-sensing mode. In some implementations, the control system may be capable of maintaining the ultrasonic transmitter 20 in an "off" state when operating the ultrasonic sensor system in a force-sensing mode. The ultrasonic receiver 30 may be capable of functioning as a force sensor when the ultrasonic sensor system 1500a is operating in the force-sensing mode. In some implementations, the control system 206 may be capable of controlling other devices, such as a display system, a communication system, etc. In some implementations, the control system 206 may be capable of operating the ultrasonic sensor system 1500a in a capacitive imaging mode.

The platen 40 may be any appropriate material that can be acoustically coupled to the receiver, with examples including plastic, ceramic, sapphire, metal and glass. In some implementations, the platen 40 may be a cover plate, e.g., a cover glass or a lens glass for a display. Particularly when the ultrasonic transmitter 20 is in use, fingerprint detection and imaging can be performed through relatively thick platens if desired, e.g., 3 mm and above. However, for implementations in which the ultrasonic receiver 30 is capable of imaging fingerprints in a force detection mode or a capacitance detection mode, a thinner and relatively more compliant platen 40 may be desirable. According to some such implementations, the platen 40 may include one or more polymers, such as one or more types of parylene, and may be substantially thinner. In some such implementations, the platen 40 may be tens of microns thick or even less than 10 microns thick.

Examples of piezoelectric materials that may be used to form the piezoelectric receiver layer 36 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF planar piezoelectric transmitter layer 22 is approximately 28 μm thick and a PVDF-TrFE receiver layer 36 is approximately 12 μm thick. Example frequencies of the ultrasonic waves may be in the range of 5 MHz to 30 MHz, with wavelengths on the order of a millimeter or less.

Figure 15B:
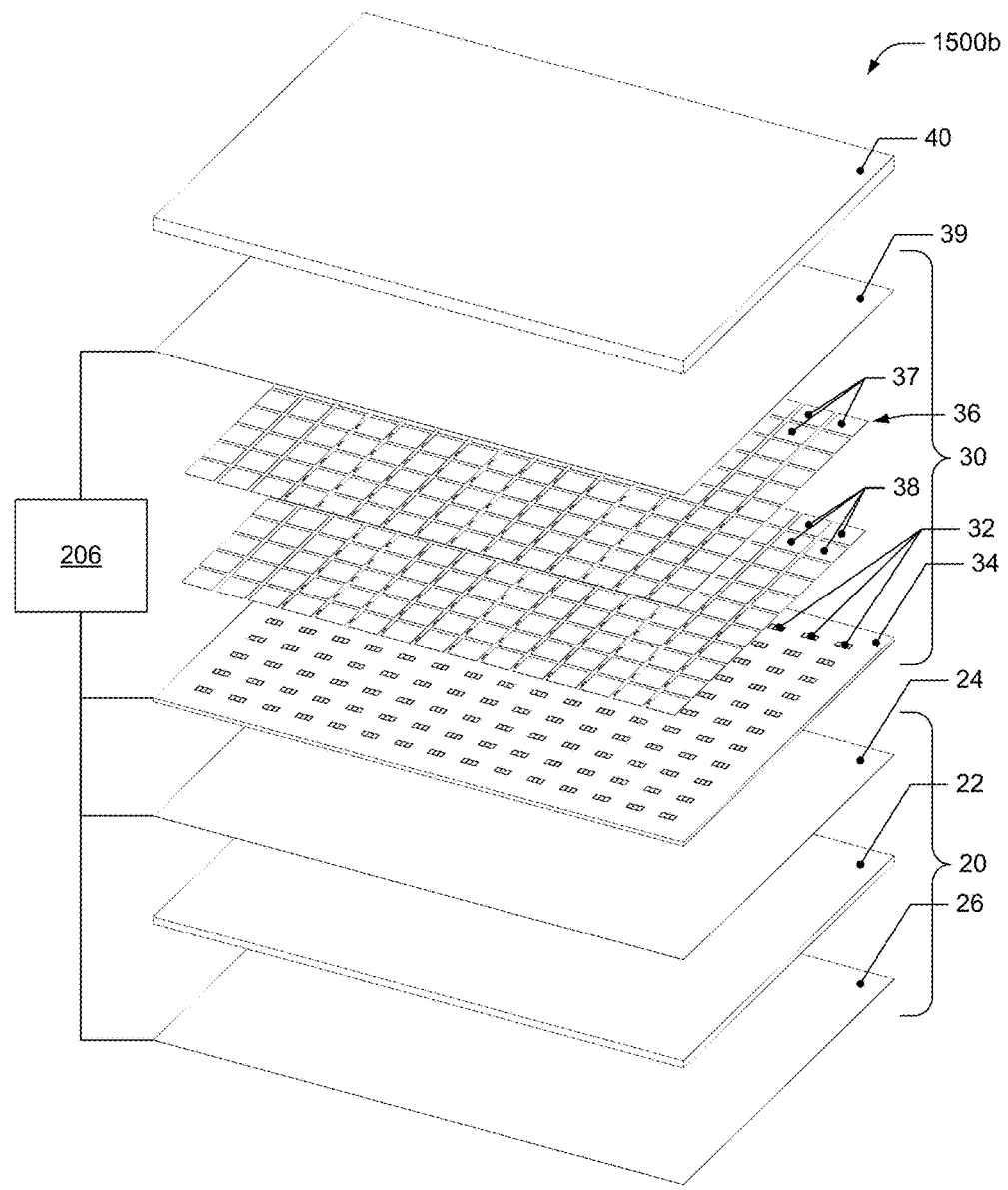
FIG. 15B shows an exploded view of an alternative example of an ultrasonic sensor system.

FIG. 15B shows an exploded view of an alternative example of an ultrasonic sensor system. In this example, the piezoelectric receiver layer 36 has been formed into discrete elements 37. In the implementation shown in FIG. 15B, each of the discrete elements 37 corresponds with a single pixel input electrode 38 and a single sensor pixel circuit 32. However, in alternative implementations of the ultrasonic sensor system 1500b, there is not necessarily a one-to-one correspondence between each of the discrete elements 37, a single pixel input electrode 38 and a single sensor pixel circuit 32. For example, in some implementations there may be multiple pixel input electrodes 38 and sensor pixel circuits 32 for a single discrete element 37.

FIGS. 15A and 15B show example arrangements of ultrasonic transmitters and receivers in an ultrasonic sensor system, with other arrangements possible. For example, in some implementations, the ultrasonic transmitter 20 may be above the ultrasonic receiver 30 and therefore closer to the object(s) 25 to be detected. In some implementations, the ultrasonic transmitter may be included with the ultrasonic sensor array (e.g., a single-layer transmitter and receiver). In some implementations, the ultrasonic sensor system may include an acoustic delay layer. For example, an acoustic delay layer may be incorporated into the ultrasonic sensor system between the ultrasonic transmitter 20 and the ultrasonic receiver 30. An acoustic delay layer may be employed to adjust the ultrasonic pulse timing, and at the same time electrically insulate the ultrasonic receiver 30 from the ultrasonic transmitter 20. The acoustic delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor system is arriving at the ultrasonic receiver 30. In some implementations, the substrate 34 and/or the platen 40 may serve as an acoustic delay layer.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

The invention claimed is:

1. An apparatus, comprising:
 an ultrasonic sensor array;
 a light source system;
 a display; and
 a control system comprising one or more general purpose single- or multi-chip processors, digital signal processors, application specific integrated circuits, field programmable gate arrays or other programmable logic devices, discrete gates, discrete transistor logic or discrete hardware components, the control system being configured to:
  control the light source system to emit light, wherein the light induces acoustic wave emissions inside a target object;
  select a first acquisition time delay for the reception of acoustic wave emissions primarily from a first depth inside the target object;
  acquire first ultrasonic image data from the acoustic wave emissions received by the ultrasonic sensor array during a first acquisition time window that is initiated at an end time of the first acquisition time delay, wherein the control system is further configured to select second through $N^{th}$ acquisition time delays and to acquire second through $N^{th}$ ultrasonic image data during second through $N^{th}$ acquisition time windows after the second through $N^{th}$ acquisition time delays, each of the second through $N^{th}$ acquisition time delays corresponding to a second through an $N^{th}$ depth inside the target object; and
  control the display to depict a three-dimensional image that corresponds with at least a subset of the first through $N^{th}$ ultrasonic image data.

2. The apparatus of claim 1, wherein the acquisition time delay is measured from a time that the light source system emits light.

3. The apparatus of claim 1, wherein the first acquisition time window is in the range of about 10 nanoseconds to about 200 nanoseconds.

4. The apparatus of claim 1 further comprising a substrate, wherein the ultrasonic sensor array is formed in or on the substrate and the light source system is coupled to the substrate.

5. The apparatus of claim 1, wherein light emitted by the light source system is transmitted through the ultrasonic sensor array.

6. The apparatus of claim 1, further comprising a display, wherein the control system is further configured to control the display to depict a two-dimensional image that corresponds with the first ultrasonic image data.

7. The apparatus of claim 1, wherein the control system is further configured to select one or more wavelengths of the light to trigger acoustic wave emissions primarily from a particular type of material in the target object.

8. The apparatus of claim 1, wherein the control system is further configured to estimate a blood oxygen level.

9. The apparatus of claim 1, wherein the control system is further configured to estimate a blood glucose level.

10. The apparatus of claim 1, wherein the control system is further configured to control the light source system to emit at least one light pulse having a duration that is in the range of about 10 nanoseconds to about 500 nanoseconds.

11. The apparatus of claim 1, wherein the light source system includes at least one backlight or front light configured for illuminating a display and the target object.

12. The apparatus of claim 1, wherein the light source system includes one or more laser diodes, semiconductor lasers or light-emitting diodes.

13. The apparatus of claim 1, wherein the light source system includes at least one infrared, optical, red, green, blue, white or ultraviolet light-emitting diode or at least one infrared, optical, red, green, blue or ultraviolet laser diode.

14. The apparatus of claim 1, wherein the control system is capable of controlling the light source system to emit a plurality of light pulses at a pulse frequency between about 1 MHz and about 100 MHz.

15. The apparatus of claim 1, wherein the first ultrasonic image data is acquired during the first acquisition time window from a peak detector circuit disposed in each of a plurality of sensor pixels within the ultrasonic sensor array.

16. The apparatus of claim 1, wherein the ultrasonic sensor array and a portion of the light source system are configured in one of an ultrasonic button, a display module, or a mobile device enclosure.

17. The apparatus of claim 1, wherein the control system is further configured to:
 acquire second ultrasonic image data at primarily the first depth inside the target object, the second ultrasonic image data acquired after the target object is repositioned on the apparatus; and
 stitch together the first and second ultrasonic image data to form a composite ultrasonic image.

18. The apparatus of claim 1, wherein the control system is further configured to acquire second ultrasonic image data primarily from the first depth inside the target object, the second ultrasonic image data acquired after a period of time corresponding to a frame rate.

19. The apparatus of claim 1, wherein the control system is further configured to acquire second ultrasonic image data from insonification of the target object with ultrasonic waves from an ultrasonic transmitter, the second ultrasonic image data acquired primarily from the first depth inside the target object, and wherein the first ultrasonic image data and the second ultrasonic image data are acquired from a plurality of sensor pixels within the ultrasonic sensor array.

20. An apparatus, comprising:
 an ultrasonic sensor array;
 a light source system; and
 control means for:
  controlling the light source system to emit light, wherein the light induces acoustic wave emissions inside a target object;
  selecting a first acquisition time delay to receive the acoustic wave emissions primarily from a first depth inside the target object;
  acquiring first ultrasonic image data from the acoustic wave emissions received by the ultrasonic sensor array during a first acquisition time window that is initiated at an end time of the first acquisition time delay, wherein the control means includes means for selecting second through $N^{th}$ acquisition time delays and of acquiring second through $N^{th}$ ultrasonic image data during second through $N^{th}$ acquisition time windows after the second through $N^{th}$ acquisition time delays, each of the second through $N^{th}$ acquisition time delays corresponding to a second through an $N^{th}$ depth inside the target object; and acquiring second ultrasonic image data from insonification of the target object with ultrasonic waves from an ultrasonic transmitter, the second ultrasonic image data acquired primarily from the first depth inside the target object, and wherein the first ultrasonic image data and the second ultrasonic image data are acquired from a plurality of sensor pixels within the ultrasonic sensor array.

21. The apparatus of claim 20, wherein the acquisition time delay is measured from a time that the light source system emits light and wherein the first acquisition time window is in the range of about 10 nanoseconds to about 200 nanoseconds.

22. The apparatus of claim 20, wherein the control means includes means for estimating a blood oxygen level.

23. The apparatus of claim 20, wherein the control means includes means for of estimating a blood glucose level.

24. The apparatus of claim 20, wherein the control means includes means for controlling the light source system to emit at least one light pulse having a duration that is in the range of about 10 nanoseconds to about 500 nanoseconds.

25. The apparatus of claim 20, further comprising a display, wherein the light source system includes at least one backlight or front light configured for illuminating the display and the target object.

26. The apparatus of claim 20, further comprising a display, wherein the control means includes means for controlling the display to depict a two-dimensional image that corresponds with the first ultrasonic image data.

27. A method of acquiring ultrasonic image data, comprising:
controlling a light source system to emit light, wherein the light induces acoustic wave emissions inside a target object;
selecting a first acquisition time delay to receive the acoustic wave emissions primarily from a first depth inside the target object; and
acquiring first ultrasonic image data from the acoustic wave emissions received by a ultrasonic sensor array during a first acquisition time window that is initiated at an end time of the first acquisition time delay;
selecting second through $N^{th}$ acquisition time delays;
acquiring second through $N^{th}$ ultrasonic image data during second through $N^{th}$ acquisition time windows after the second through $N^{th}$ acquisition time delays, each of the second through $N^{th}$ acquisition time delays corresponding to a second through an $N^{th}$ depth inside the target object; and
controlling a display to depict a three-dimensional image that corresponds with at least a subset of the first through $N^{th}$ ultrasonic image data.

28. The method of claim 27, wherein the acquisition time delay is measured from a time that the light source system emits light and wherein the first acquisition time window is in the range of about 10 nanoseconds to about 200 nanoseconds.

29. The method of claim 27, further comprising controlling a display to depict a two-dimensional image that corresponds with the first ultrasonic image data.

30. A non-transitory medium having software stored thereon, the software including instructions for controlling one or more devices for:
controlling a light source system to emit light, wherein the light induces acoustic wave emissions inside a target object;
selecting a first acquisition time delay to receive the acoustic wave emissions primarily from a first depth inside the target object; and
acquire first ultrasonic image data from the acoustic wave emissions received by a ultrasonic sensor array during a first acquisition time window that is initiated at an end time of the first acquisition time delay;
selecting second through $N^{th}$ acquisition time delays;
acquiring second through $N^{th}$ ultrasonic image data during second through $N^{th}$ acquisition time windows after the second through $N^{th}$ acquisition time delays, each of the second through $N^{th}$ acquisition time delays corresponding to a second through an $N^{th}$ depth inside the target object; and
acquiring second ultrasonic image data from insonification of the target object with ultrasonic waves from an ultrasonic transmitter, the second ultrasonic image data acquired primarily from the first depth inside the target object, and wherein the first ultrasonic image data and the second ultrasonic image data are acquired from a plurality of sensor pixels within the ultrasonic sensor array.

31. The non-transitory medium of claim 30, wherein the acquisition time delay is measured from a time that the light source system emits light and wherein the first acquisition time window is in the range of about 10 nanoseconds to about 200 nanoseconds.

32. The non-transitory medium of claim 30, wherein the software includes instructions for controlling a display to depict a two-dimensional image that corresponds with the first ultrasonic image data.

* * * * *